(12) United States Patent
Dorothee et al.

(10) Patent No.: US 10,183,061 B2
(45) Date of Patent: Jan. 22, 2019

(54) BOOSTING TREG CELLS FOR TREATING ALZHEIMER DISEASE AND RELATED DISORDERS

(71) Applicants: ICM (INSTITUT DU CERVEAU ET DE LA MOELLE EPINIERE), Paris (FR); APHP (ASSISTANCE PUBLIQUE-HOPITAUX DE PARIS), Paris (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR); UNIVERSITE PIERRE ET MARIE CURIE-PARIS 6 (UPMC), Paris (FR)

(72) Inventors: Guillaume Dorothee, Fontenay-sous-Bois (FR); Eliane Piaggio, Paris (FR); Dylla Ait Ahmed, Paris (FR); Pierre Aucouturier, Montreuil (FR)

(73) Assignees: ICM (INSTITUT DU CERVEAU ET DE LA MOELLE EPINIERE), Paris (FR); APHP (ASSISTANCE PUBLIQUE-HOPITAUX DE PARIS), Paris (FR); CENTRE NATIONAL DE LA RECHERCHE SCIENTIFIQUE (CNRS), Paris (FR); INSERM (INSTITUT NATIONAL DE LA RECHERCHE MEDICALE), Paris (FR); SORBONNE UNIVERSITE, Paris (FR)

( * ) Notice: Subject to any disclaimer, the term of this patent is extended or adjusted under 35 U.S.C. 154(b) by 0 days.

(21) Appl. No.: 14/392,315

(22) PCT Filed: Jun. 20, 2014

(86) PCT No.: PCT/EP2014/063080
§ 371 (c)(1),
(2) Date: Dec. 24, 2015

(87) PCT Pub. No.: WO2014/206899
PCT Pub. Date: Dec. 31, 2014

(65) Prior Publication Data
US 2016/0287671 A1 Oct. 6, 2016

Related U.S. Application Data

(60) Provisional application No. 61/838,984, filed on Jun. 25, 2013.

(30) Foreign Application Priority Data

Jun. 25, 2013 (EP) .................................. 13173617

(51) Int. Cl.
A61K 38/20 (2006.01)
A61K 45/06 (2006.01)
C07K 14/55 (2006.01)
A61K 39/00 (2006.01)

(52) U.S. Cl.
CPC .......... *A61K 38/2013* (2013.01); *A61K 38/20* (2013.01); *A61K 45/06* (2013.01); *A61K 2039/545* (2013.01); *C07K 14/55* (2013.01)

(58) Field of Classification Search
CPC .... A61K 38/2013; A61K 38/20; A61K 45/06; A61K 2121/00; A61K 2039/545; C07K 14/55
See application file for complete search history.

(56) References Cited

U.S. PATENT DOCUMENTS

| 4,530,787 A | 7/1985 | Shaked et al. |
| 4,604,377 A | 5/1986 | Fernandes et al. |
| 4,656,132 A | 4/1987 | Ben-Bassat et al. |
| 4,748,234 A | 5/1988 | Dorin et al. |
| 4,752,585 A | 6/1988 | Koths et al. |
| 6,579,521 B2 * | 6/2003 | Sahner ............... A61K 31/7068 424/85.2 |
| 2005/0260767 A1 | 11/2005 | Clerici et al. |
| 2013/0028861 A1 * | 1/2013 | Huland .................. A61K 9/007 424/85.2 |
| 2014/0356319 A1 * | 12/2014 | Penton Rol .............. C07K 5/08 424/85.2 |
| 2017/0020962 A1 * | 1/2017 | Klatzmann ............ A61K 38/20 |

FOREIGN PATENT DOCUMENTS

| EP | 109748 | 10/1982 |
| EP | 136489 | 8/1983 |
| EP | 118617 | 9/1984 |
| EP | 200280 | 11/1986 |
| WO | 2012123381 | 9/2012 |

(Continued)

OTHER PUBLICATIONS

Baek H et al. Neuroprotective effects of CD4+CD25+Foxp3+ regulatory T cells in a 3xTg-AD Alzheimer's disease model. Oncotarget, 2016, 7(43):69347-69357.*
Dansokho C et al. Regulatory T cells delay disease progression in Alzheimer-like pathology. Brain, 2016, 139:1237-1251.*
Liu R et al. Expansion of regulatory T cells via IL-2/anti-IL-2 mAb complexes suppresses experimental myasthenia. Eur. J. Immunol. 2010, 40:1577-1589.*
Eggena MP et al. Depletion of regulatory T cells in HIV infection is associated with immune activation. J. Immunol. 174:4407-4414. (Year: 2005).*
Pellicano M et al. Immune profiling of Alzheimer patients. J. Neuroimmunol. 242:52-59. (Year: 2012).*

(Continued)

Primary Examiner — Kimberly Ballard
(74) Attorney, Agent, or Firm — Young & Thompson

(57) ABSTRACT

The present invention relates to the boosting of Treg cells for the treatment of Alzheimer's disease and related disorders.

56 Claims, 11 Drawing Sheets

(56) References Cited

FOREIGN PATENT DOCUMENTS

WO     WO 2013004203 A1 * 1/2013 ............... C07K 5/08

OTHER PUBLICATIONS

Rosenkranz D et al. Higher frequency of regulatory T cells in the elderly and increased suppressive activity in neurodegeneration. J. Neuroimmunol. 188:117-127. (Year: 2007).*

Cao C et al. Abeta-specific Th2 cells provide cognitive and pathological benefits to Alzheimer's mice without infiltrating the CNS. Neurobiol. Dis. 34(1):63-70. (Year: 2009).*

Venuprasad Poojary K et al. Control of Th2-mediated inflammation by regulatory T cells. Am. J. Pathol. 177(2):525-531. (Year: 2010).*

Garcia et al. Phase I/II trial of subcutaneous interleukin-2, granulocyte-macrophage colony-stimulating factor and interferon-alpha in patients with metastatic renal cell carcinoma. BJUI, 109:63-69. (Year: 2011).*

Rosenkranz et al., "Higher frequency of regulatory T cells in the elderly and increased suppressive activity in neurodegeneration", 2007, Journal of Neuroimmunology 188 (1-2): 117-127.

Toly-Ndour et al., "MHC-Independent Genetic Factors Control the Magnitude of CD4+ T Cell Responses to Amyloid-β Peptide in Mice through Regulatory T Cell-Mediated Inhibition", Nov. 1, 2011, Journal of Immunology, ; 187 (9):4492-4500.

Avidan et al., "Vaccination with autoantigen protects against aggregated beta-amyloid and glutamate toxicity by controlling microglia: effect of CD4+CD25+ T cells", Eur. J. Immunol. Dec. 2004;34(12):3434-3445.

Petitto et al., "Interleukin-2 and the Septohippocampal System: Intrinsic Actions and Autoimmune Processes Relevant to Neuropsychiatric Disorders", 2012, Methods in Molecular Biology, 829:433-443.

Lacosta et al., "Influence of Acute and Repeated Interleukin-2 Administration on Spatial Learning, Locomotor Activity, Exploratory Behaviors, and Anxiety", 1999, Behavioral Neuroscience, 113(5):1030-1041.

Citron, "Alzheimer's disease: strategies for disease modification", Nature Reviews, Drug Discovery, May 2010;9(5):387-398.

Radde et al., "Abeta42-driven cerebral amyloidosis in transgenic mice reveals early and robust pathology", EMBO Reports, Sep. 2006;7(9):940-946.

International Search Report of PCT/EP2014/063080 dated Jul. 30, 2014.

* cited by examiner

A

B

A

B

BOOSTING TREG CELLS FOR TREATING ALZHEIMER DISEASE AND RELATED DISORDERS

FIELD OF INVENTION

The present invention relates to the boosting of Treg cells for the treatment of Alzheimer's disease and related disorders.

BACKGROUND OF INVENTION

Alzheimer's disease (AD) is a neurodegenerative disorder characterized by progressive loss of memory and cognitive functions. Accumulation of Aβ peptide is considered the initiating cause of pathogenic lesions, and vaccination against Aβ provided encouraging results in mouse models of the disease. However, in a first clinical trial of immunization against Aβ, 6% of the patients developed meningoencephalitis attributed to vaccine-induced brain-infiltrating pro-inflammatory T cells. On the other hand, Aβ-specific CD4$^+$ T cells may be implicated in the natural course of AD and their modulation could result in a strong therapeutic effect.

The magnitude of Aβ-specific CD4$^+$ T cell responses is controlled by regulatory T cells (Tregs) in both physiological and pathological settings in response to Aβ vaccination (Toly-Ndour C et al. 2011 J. Immunol. November 1; 187 (9):4492-500).

Therefore, Tregs could constitute an interesting target for treating Alzheimer's disease and related disorders.

The literature suggested so far that weakening the activity of Treg cells would be a good therapeutic strategy to treat Alzheimer's disease and related disorders. Indeed, Rosenkranz et al. (2007 J Neuroimmunol. 188:117-127) observed that Treg activity was increased in patients with Alzheimer's disease. Moreover, Avidan et al. (2004 Eur J Immunol 34:3434-3445) found that Treg down regulate the ability of the neural tissue to resist to Aβ toxicity.

In addition, several studies found that a renowned booster of Treg cells, IL-2, induced cognitive dysfunction and neuropsychiatric side effects in some patients treated for cancer (Petitto J M et al. 2012 Methods Mol Biol. 829:433-43; Lacosta S et al. 1999 Behav. Neurosc. 113(5):1030-1041).

Consequently, the literature suggested to the patrician 1) inhibiting the Treg cells for treating AD and 2) not using IL-2 for treating a neurodegenerative disease as it causes neurological dysfunctions and side effects.

Surprisingly, the inventors found that depletion of Tregs cells accelerated the onset of cognitive deficits in a mouse model of AD, the APPPS1 mice. Alteration in spatial memory is then detectable at 7 months in Treg-depleted APPPS1 mice, i.e. earlier as compared to untreated APPPS1 mice. In addition, the inventors showed a beneficial role of boosted-Tregs cells in the pathophysiology of AD: indeed, administration of low doses of IL-2 in APPPS1 mice delayed the development of Alzheimer's disease and related disorders.

SUMMARY

One object of the invention is a booster of Treg cells for use in treating an Alzheimer's disorder.

In one embodiment, the booster is low dose IL-2

Another object of the invention is a pharmaceutical composition for use in treating an Alzheimer's disorder, said pharmaceutical composition comprising the booster as described here above, and a pharmaceutically acceptable excipient.

In one embodiment, said pharmaceutical composition further comprises one or more active agent(s) for treating an Alzheimer's disorder and/or side effects of said active agent(s).

In another embodiment, said pharmaceutical composition comprises IL-2 at a low dose.

In another embodiment, said pharmaceutical is to be administered to the subject in need thereof at dose ranged below 3.5 MIU/m$^2$/day.

In another embodiment, a therapeutically effective amount of the pharmaceutical composition is to be administered prior to, concurrent to, or subsequent to other active agent(s) for use in treating an Alzheimer's disorder and/or side effects of said active agent(s).

In another embodiment, said pharmaceutical composition is to be administered to the subject in need thereof by subcutaneous, intramuscular, intravenous, intraocular, transdermal, topical, parenteral, rectal, intranasal and oral administration, or injection.

In another embodiment, the subject to be treated is at an early timing stage of an Alzheimer's disorder.

In another embodiment, the subject to be treated is at risk of developing an Alzheimer's disorder.

In another embodiment, the subject to be treated is diagnosed with an Alzheimer's disorder.

In another embodiment, the subject to be treated presents a genetic predisposition to Alzheimer's disease and related disorders or at risk to develop an Alzheimer's disorder.

In another embodiment, the subject to be treated is affected, preferably diagnosed, with an early-onset variant of an Alzheimer's disorder.

Another object of the invention is a method for determining whether a low dose IL-2 treatment has to be modified in a subject treated with IL-2, which method comprises monitoring the quantity of Tregs and/or CD25$^+$ and/or Foxp3$^+$ and/or CD127$^-$ and/or PD1$^-$ expression level in subjects.

Definitions

In the present invention, the following terms have the following meanings:

"Alzheimer's disease and related disorders" can also be referred as an Alzheimer's disorder, Alzheimer's disease and Alzheimer's-like disorders and refers to progressive cognitive and functional impairments of the brain. Early symptoms can affect the most complex daily living activities. The most noticeable deficit is a cognitive deficit, which shows up as difficulty in remembering recently learned facts and inability to acquire new information. Alzheimer's disorders include amyloid-related disorders such as: mild cognitive impairment; vascular dementia; early Alzheimer's disease; Alzheimer's disease, including sporadic (non-hereditary) Alzheimer's disease and familial (hereditary) Alzheimer's disease; age-related cognitive decline; posterior cortical atrophy (or Benson syndrome); logopenic progressive primary aphasia; cerebral amyloid angiopathy ("CAA"); Lewy body disease; hereditary cerebral hemorrhage; Down's syndrome; inclusion body myositis ("LBM"); or age-related macular degeneration ("ARMD"); Tau-related pathologies such as: Progressive supranuclear palsy; corticobasal syndrome; Dementia pugilistica (chronic traumatic encephalopathy); Lytico-Bodig disease; Tanglepredominant dementia; Ganglioglioma and gangliocytoma; Hallervorden-Spatz disease; lipofuscinosis; Argyrophilic grain disease (AGD); Frontotemporal lobar degeneration (FTLD), including behavioural variant of Frontotemporal dementia, progressive non-fluent aphasia, semantic dementia; Lewy body-related disorders. The symptoms are but not limited to: memory loss (recent memory, personal history, conversations . . . ), cognitive deficits, behavioral and mood changes, depression, apathy.

"Treg cells" refers to a subpopulation of T cells that modulate the immune system, maintain tolerance to self-antigens, and abrogate autoimmune diseases. T regulatory cells are a component of the immune system that suppresses immune responses of other cells. Regulatory T cells come in many forms with the most well-understood being those that express CD4, CD25, and Foxp3.

"Treatment" refers to therapeutic treatment, prophylactic or preventative measures and deferment of the disease onset; wherein the object is to delay, prevent or slow down (lessen) the targeted pathologic condition or disorder. Those in need of treatment include those already with Alzheimer's disorders, as well as those prone to have an Alzheimer's disorder, or those in whom an Alzheimer's disorder is to be prevented or delayed. A subject or mammal is successfully "treated" for an Alzheimer's disorder if, after receiving a therapeutic amount of a composition according to the invention, the patient shows observable and/or measurable Treg cells boosting, reduction in cognitive deficits, and/or improvement in quality of life issues. The above parameters for assessing successful treatment and improvement in the disease are readily measurable by routine procedures familiar to a physician.

"Subject" refers to a mammal, preferably a human. In one embodiment, the subject is female. In another embodiment, the subject is male.

"Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, and general safety and purity standards as required by FDA Office of Biologics standards.

"Therapeutically effective amount" refers to the level or amount of agent that is aimed at, without causing significant negative or adverse side effects to the target, delaying or preventing the onset of an Alzheimer's disorder; slowing down or stopping the progression, aggravation, or deterioration of one or more symptoms of an Alzheimer's disorder; bringing about ameliorations of the symptoms of Alzheimer's disorders; reducing the severity or incidence of an Alzheimer's disorder; or curing an Alzheimer's disorder. An effective amount may be administered prior to the onset of an Alzheimer's disorder, for a delayed, prophylactic or preventive action. Alternatively or additionally, the effective amount may be administered after initiation of an Alzheimer's disorder, for a therapeutic action.

"Low dose IL-2" refers to the level or amount of agent that boosts Treg cells (that can be quantified by determining $CD4^+$, $CD25^+$ and/or Foxp3, $PD1^-$ and/or $CD127^-$ expression) without substantially inducing and/or stimulating effector T lymphocytes.

"Boosting of Treg", "Booster of Treg" refers to the amplification of the pool of Treg cells, the improvement of Treg cells survival, the improvement of the functionality of Treg cells, without substantial amplification of the pool of effector T cells and/or B cells.

DETAILED DESCRIPTION

This invention relates to a booster of Tregs cells for use in treating an Alzheimer's disorder.

In one embodiment of the invention, the booster of Treg cells amplifies selectively the pool of Treg cells.

In one embodiment of the invention, the booster of Treg cells increases the survival of Treg cells.

In one embodiment of the invention, the booster of Treg cells improves the functionality of Treg cells.

In another embodiment of the invention, the booster of Treg cells does not amplify effector T cells (Teff).

In another embodiment of the invention, the booster of Treg cells does not amplify B cells.

In another embodiment of the invention, the booster of Treg cells increases the ratio Treg/Teff.

Within the context of this invention, a boosting of Treg cells refers to any increase in proportion of Treg cells relative to Teffs, in number or in activity as tested by suppressive assays or by expression of molecules that reflect the activity of the Tregs such as CD25, the alpha-chain of the IL-2 receptor, in a subject. The augmentation in proportion is preferably by at least 10%, 20%, 30%, 40%, 50%, 60% as compared to the level prior to treatment. In one embodiment, the boosting designates a shift in the Treg/Teff balance towards Tregs, or an increase in the Treg/Teff ratio.

The boosting of Tregs can be determined by measuring the number of Tregs (e.g., based on the expression of CD25, FoxP3, CDU27, PD1 . . . ) and/or the activity of Tregs in samples from the treated subject. The absence of substantial boosting of Teff can also be determined by measuring the number of Teff and/or the activity of Teff in samples from the treated subject. Preferably, the absence of substantial boosting of Teff indicates the target Teff cell population does not acquire markers of activation such as CD25, CD69, and/or HLA-DR, or as assessed by whole transcriptome analyses. Detailed methods for detecting, measuring and quantifying Treg and Teff cells are well known per se in the art. In one embodiment, the boosting of Treg cells is performed as in Example 3 described here below.

In one embodiment, the invention increases circulating $CD4^+$ $CD25^{hi}$ $CD127^-$ $Foxp3^+$ Tregs.

In one embodiment, the invention increases circulating $CD4^+$ $CD25^{hi}$ $CD127^-$ $Foxp3^+$ $PD1^-$ Tregs.

In one embodiment, the invention increases circulating $CD8^+$ $CD25^{hi}$ $Foxp3^+$ Tregs.

In one embodiment of the invention, the booster of Tregs cells includes but is not limited to: IL-2.

In one embodiment of the invention, the booster of Tregs cells is IL-2 and most preferably a low dose of IL-2.

The present invention also relates to a medicament for use in treating an Alzheimer's disorder in a subject in need thereof, comprising the booster of Tregs cells as described herein.

One object of the present invention is a pharmaceutical composition for use in treating an Alzheimer's disorder in a subject in need thereof, said pharmaceutical composition comprising a booster of Tregs as described herein and a pharmaceutically acceptable excipient.

In one embodiment of the present invention, the pharmaceutical composition may comprise IL-2.

In one embodiment of the invention, IL-2 is native or obtained by recombinant or synthetic techniques. IL-2 may be or comprise the native polypeptide sequence, or can be an active variant of the native IL-2 polypeptide. IL-2 is obtained from different sources including mammalian sources such as e.g., human, mouse, rat, primate, and pig.

In one embodiment of the invention, the IL-2 polypeptide or active variant is derived from a human source, and includes recombinant human IL-2, particularly recombinant human IL-2 produced by microbial hosts. Active variants of IL-2 have been disclosed in the literature.

In one embodiment of the invention. IL-2 is a variant of the native IL-2, which can be fragments, analogues, and derivatives thereof. "Fragment" refers to a polypeptide comprising only a part of the intact polypeptide sequence. An "analogue" designates a polypeptide comprising the native polypeptide sequence with one or more amino acid substitutions, insertions, or deletions. Muteins and pseudopeptides are specific examples of analogues. "Derivatives" refers to any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). Active variants of a reference IL-2 polypeptide generally have at least 75%, preferably at least 85%, more preferably at least 90% amino acid sequence identity to the amino acid sequence of the reference IL-2 polypeptide. Methods for determining whether a variant IL-2 polypeptide is active are available in the art. An active variant is, most preferably, a variant that boosts Treg cells.

Examples of IL-2 variants are disclosed, for instance, in EP109748, EP136489, U.S. Pat. No. 4,752,585; EP200280, or EP118,617.

In one embodiment of the invention, IL-2 is a recombinant IL-2, such as for example, an IL-2 that has been prepared by recombinant DNA techniques. The host organism used to express a recombinant DNA encoding IL-2 may be prokaryotic (a bacterium such as *E. coli*) or eukaryotic (e.g., a yeast, fungus, plant or mammalian cell). Processes for producing IL-2 have been described e.g., in U.S. Pat. No. 4,656,132; U.S. Pat. No. 4,748,234; U.S. Pat. No. 4,530,787; or U.S. Pat. No. 4,748,234, incorporated therein by reference. In a preferred embodiment, the invention uses an IL-2 of human origin, or an active variant thereof, more preferably produced recombinantly. A nucleotide and an amino acid sequence of human IL-2 are disclosed, for instance, in Genbank ref 3558 or P60568, respectively.

In one embodiment of the invention, IL2 is a human IL-2. IL-2 for use in the present invention shall be in essentially pure form, e.g., at a purity of 95% or more, further preferably 96, 97, 98 or 99% pure. For use in the present invention, IL-2 is administered alone.

In one embodiment of the invention, the IL2 is in monomeric or multimeric form.

IL-2 is commercially available, including for pharmaceutical uses, and it is authorized for use in human patients. Examples of IL-2 include but are not limited to: Proleukin®, Aldesleukin®, Roncoleukin®.

Specific examples of IL-2 formulations are described in U.S. Pat. No. 4,604,377.

Where IL-2 is in monomeric form, it is preferred to add to the compositions an amino acid base sufficient to decrease aggregation of IL-2 during storage. The amino acid base can be an amino acid or a combination of amino acids, where any given amino acid is present either in its free base form or in its salt form. Examples of such amino acids include arginine, lysine, and aspartic acid. In a particular embodiment, the composition comprises a multimeric IL-2, for example lyophilized.

A specific example of such a composition is Proleukin® IL-2. This lyophilized formulation comprises selectively oxidized, recombinant IL-2 admixed with a water soluble carrier, such as mannitol, that provides bulk, and SDS to ensure solubility of IL-2 in water. This composition is suitable for reconstitution in aqueous solutions for parenteral injection.

The current packaging of IL-2 is vials containing 18 M IU of IL-2. Given the low dose to be used, packaging for dose of 0.01 MIU, 0.02 MIU, 0.5 MIU 0.1 MIU, 0.2 MIU, 0.5 MIU, 1 MIU and 3, or 3.5 MIU are preferably prepared.

Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment of the invention, the pharmaceutical composition is administered at a therapeutically effective amount. It corresponds to the amount of a therapeutic agent necessary and sufficient for delaying the onset, preventing, slowing down or stopping the progression, aggravation, or deterioration of one or more symptoms of Alzheimer's disorder; curing the Alzheimer's disorder.

In another embodiment of the invention, the pharmaceutical composition of the invention is administered at a dose determined by the skilled artisan and personally adapted to each subject.

The composition, pharmaceutical composition or medicament of the invention may be administered by several routes of administration. Examples of adapted routes of administration include, but are not limited to, subcutaneous, intramuscular, intravenous, intraocular, transdermal, topical, parenteral, intranasal, rectal and oral administration, or injection.

According to an embodiment, the composition, pharmaceutical composition or medicament of the invention is in a form adapted for injection, preferably selected from the group comprising solutions, such as, for example, isotonic solution, saline solution, sterile aqueous solutions, dispersions, emulsions, suspensions, solid forms suitable for using to prepare solutions or suspensions upon the addition of a liquid prior to use, such as, for example, powder, freeze-dried compositions, liposomal forms and the like.

According to an embodiment, the composition, pharmaceutical composition or medicament of the invention is in a form adapted to oral administration. According to a first embodiment, the form adapted to oral administration is a solid form selected from the group comprising tablets, pills, capsules, soft gelatin capsules, sugarcoated pills, orodispersing/orodispersing tablets, effervescent tablets or other solids. According to a second embodiment, the form adapted to oral administration is a liquid form, such as, for example, a drinkable solution, a buccal spray, liposomal forms and the like.

According to an embodiment, the composition, pharmaceutical composition or medicament of the invention is in a form adapted for local delivery via the nasal and respiratory routes. Examples of formulations suitable for nasal administration include but are not limited to, nasal solutions, sprays, aerosols and inhalants.

According to an embodiment, the composition, pharmaceutical composition or medicament of the invention is in a form adapted to topical administration. Examples of formulations adapted to topical administration include, but are not limited to, ointment, paste, eye drops, cream, patch, such as, for example, transdermal patch, gel, liposomal forms and the like.

According to an embodiment, the composition, pharmaceutical composition or medicament of the invention is in the form of, or comprises, liposomes and/or nanoparticles.

In another embodiment of the invention, the composition, pharmaceutical composition or medicament of the invention is administered at a low dose.

In one embodiment of the invention, the composition, the pharmaceutical composition or the medicament of the invention is administered at a dosage that effectively boosts Tregs cells without substantially boosting effector T cells (Teff). The consequence is a dramatic increase in the Treg/Teff balance in the subject.

The effective dosage can be adjusted by the practitioner, based on information contained in the present application. In particular, with the knowledge of the present invention that, in patients with Alzheimer's disorder, IL-2 may be administered under conditions that do activate Tregs without substantially activating Teff, the skilled person may be able to adjust dosages to each patient and condition. Typically, IL-2 is administered at a dose of about 0.05 to about 2 MIU/m$^2$/day, preferably 0.2 to about 1 MIU/m$^2$/day.

The amount of IL-2 to administer thus preferably depends on the body surface area of the subject. The body surface area (BSA) is the measured or calculated surface of a human body. Various calculations have been published to determine the BSA without direct measurement: The Dubois & Dubois formula is commonly used in adults:

$$BSA(m^2) = 0.007184 \times weight(kg)^{0.425} \times height(cm)^{0.725} = \frac{weight(kg)^{0.425} \times height(cm)^{0.725}}{139.2}$$

Another commonly used formula is the Mosteller formula adopted for use by the Pharmacy and Therapeutics Committee of the Cross Cancer Institute, Edmonton, Alberta, Canada:

$$BSA(m^2) = \sqrt{\frac{weight(kg) \times height(cm)}{3600}} = \frac{weight(kg)^{0.5} \times height(cm)^{0.6}}{60}$$

It is more particularly used in children.

Average BSA is generally taken to be 1.73 m$^2$ for an adult. Average BSA values are the following: Neonate (Newborn) 0.25 m$^2$, Child 2 years 0.5 m$^2$, Child 9 years 1.07 m$^2$, Child 10 years 1.14 m$^2$, Child 12-13 years 1.33 m$^2$, Men 1.9 m$^2$, Women 1.6 m$^2$.

Typically, the dosage according to the invention is below 3.5 Million IU/day/subject, below 3.0 Million IU/day/subject, below 2.5 Million IU/day/subject, below 2.0 Million IU/day/subject, below 1.5 MUI/day/subject, below 1 MUI/day/subject, below 0.5 MUI/day/subject.

The treatment is typically repeated, i.e., the above low doses of IL-2 are administered several times to a subject, to progressively achieve the most substantial benefit. The dose and schedule of administration vary according to the deferment, preventive or therapeutic aim of the treatment, as well as to the disease to be treated/prevented/delayed. Treatment effect can be monitored by Treg measurements and dose and administration schedule adjusted accordingly.

Exemplary dosages are between 0.1 to 3 MIU, between 0.1 to 1.5 MIU, between 0.25 to 1 MIU. Preferred dosages are: 3.0 MIU/day/subject, 2.5 MIU/day/subject, 2.0 MIU/day/subject, 1.5 MIU/day/subject, 1.0 MIU/day/subject, 0.5 MIU/day/subject, 0.3 MIU/day/subject, 0.1 MIU/day/subject, 0.05 MIU/day/subject, 0.02 MIU/day/subject, or 0.01 MIU/day/subject.

In one embodiment of the invention, IL-2 is administered at a dose of about 0.05 to about 2 MIU/m$^2$/day, preferably 0.2 to about 1 MIU/m$^2$/day.

These dosages may be combined, depending on the subject and evolution of the disease.

In one embodiment of the invention, low dose IL-2 is administered for a chronic treatment.

In another embodiment of the invention, low dose IL-2 is administered for an acute treatment.

In one embodiment of the invention, IL-2 is administered from 1 to 7 days of daily administration, preferably between 3 to 5 days. Such treatment courses may be reproduced at different time periods, interrupted by periods with no treatment.

In one embodiment of the invention. IL-2 is administered once per day during at least 3 consecutive days, preferably during 3 to 7, more preferably during 4 to 5 consecutive days, more preferably followed by a maintenance dose after 1 to 4 weeks.

In a preventive setting, IL-2 may be administered at the above dosage in single shots, at different time intervals, e.g., once a week over long periods of time. Different protocols may be adjusted depending on the subject and disease. Maintenance dosage can be administered from two to eight weeks after the initiating cycle is completed. Preferably the maintenance dose is the same as the initiating dose.

In one embodiment of the invention, the composition, pharmaceutical composition or medicament of the invention is administered at an early stage of an Alzheimer's disorder.

In another embodiment of the invention, the composition, pharmaceutical composition or medicament of the invention is administered at a mild stage of an Alzheimer's disorder.

In another embodiment of the invention, the composition, pharmaceutical composition or medicament of the invention is administered at a moderate stage of an Alzheimer's disorder.

In another embodiment of the invention, the composition, pharmaceutical composition or medicament of the invention is administered at a mild to moderate stage of an Alzheimer's disorder.

In another embodiment of the invention, the composition, pharmaceutical composition or medicament of the invention is administered at an advanced stage of an Alzheimer's disorder.

In another embodiment of the invention, the composition, pharmaceutical composition or medicament of the invention is administered at a pre-dementia stage.

In another embodiment of the invention, the composition, pharmaceutical composition or medicament of the invention is administered at a pro-dromal stage.

In another embodiment of the invention, the composition, pharmaceutical composition or medicament of the invention is administered at a stage of mild cognitive impairment.

In another embodiment of the invention, the composition, pharmaceutical composition or medicament of the invention is administered prior to Aβ plaques formation in the brain.

In another embodiment of the invention, the composition, pharmaceutical composition or medicament of the invention is administered concurrent to Aβ plaques formation in the brain.

In another embodiment of the invention, the composition, pharmaceutical composition or medicament of the invention is administered posterior to the apparition of Aβ plaques in the brain.

In another embodiment of the invention, the composition, pharmaceutical composition or medicament of the invention is administered prior cognitive deficits.

In another embodiment of the invention, the composition, pharmaceutical composition or medicament of the invention is administered prior the onset of an Alzheimer's disorder.

In one embodiment of the invention, a therapeutically effective amount of the booster is administered in a sustained-release form.

In one embodiment of the invention, the composition comprises a delivery system that controls the release of the booster.

Examples of suitable carriers for sustained or delayed release include, but are not limited to, gelatin; gum Arabic; xanthane polymers; thermoplastic resins such as, for example polyvinyl halides, polyvinyl esters, polyvinylidene halides and halogenated polyolefins; elastomers such as, for example, *brasiliensis*, polydienes, and halogenated natural and synthetic rubbers; and flexible thermoset resins such as polyurethanes, epoxy resins; biodegradable polymers and the like.

In another embodiment of the invention, a therapeutically effective amount of the composition, pharmaceutical composition or medicament of the invention is administered in combination with an effective amount of one or more other active agent(s) for treating an Alzheimer's disorder and/or an effective amount of one or more other active agent(s) for preventing side effects enhanced by said active agent(s).

In another embodiment of the invention, the composition, pharmaceutical composition or medicament of the invention is co-formulated with other active agent(s) for treating an Alzheimer's disorder and/or an effective amount of one or more other active agent(s) for preventing side effects enhanced by said active agent(s).

In one embodiment of the invention, the composition, pharmaceutical composition or medicament of the invention may be administered separately or in conjunction with other active agent(s) for treating an Alzheimer's disorder and/or an effective amount of one or more other active agent(s) for preventing side effects enhanced by said active agent(s).

In another embodiment of the invention, the composition, pharmaceutical composition or medicament of the invention may be administered prior to, concurrent to, or subsequent to the administration of other active agent(s) for treating an Alzheimer's disorder and/or an effective amount of one or more other active agent(s) for preventing side effects enhanced by said active agent(s).

In one embodiment of the invention, the composition, pharmaceutical composition or medicament of the invention may be administered to a subject in period of pre-exposure and/or post-exposure with other agent(s) for treating an Alzheimer's disorder and/or an effective amount of one or more other active agent(s) for preventing side effects enhanced by said active agent(s).

In one embodiment, the composition, pharmaceutical composition or medicament of the invention is for preventing, reducing or alleviating the symptoms associated with an Alzheimer's disorder.

In one embodiment, the composition, pharmaceutical composition or medicament of the invention is for delaying the onset of an Alzheimer's disorder.

In one embodiment of the invention, examples of the active agent(s) for treating an Alzheimer's disorder include, but are not limited to: a cholinesterase inhibitor, such as donepezil, galantamine, rivastigmine and tacrine; a N-methyl D-aspartate (NMDA) antagonist, such as memantine; a BACE 1 inhibitor such as KMI-420, KMI-429, KMI-358, KMI-370, TAK-070, and GSK188909, as reviewed, for example in Guo, T., and Hobbs, D. W., Curr. Med. Chem., vol. 13, no. 15, 2006, 1811-29; Evin, G., et al., Recent Pat CNS Drug Discov., vol. 6, no. 2, 2011, 91-106, and Citron, M., Nat Rev Drug Discov., vol. 9, 2010, 387-398, which are hereby incorporated by reference and form part of the disclosure; γ secretase inhibitors such as LY450139; passive anti-Aβ immunotherapy in the form of monoclonal anti-Aβ antibodies, such as but not limited to Bapineuzumab, Solanezumab, Gantenerumab; intravenous immunoglobulin; IV Ig (10%); intravenous Ig (IgG antibodies); Gammagard™ IV Ig (10%); PF-04360365; R1450; GSK933766A; active anti-Aβ immunotherapy such as but not limited to ACC-001, CAD-105, CAD-106, Affitope AD01, Affitope AD02, V950, UB311; non-steroidal anti-inflammatory drugs (NSAIDs); drugs enhancing Aβ clearance such as but not limited to PF-04494700; drugs inhibiting Aβ aggregation such as but not limited to ELND005, PBT2; drugs reducing Tau phosphorylation, such as but not limited to inhibitors of CDK5R1, MARK1, GSK3; passive anti-Tau immunotherapy in the form of monoclonal anti-Tau antibodies; active anti-Tau immunotherapy; APOE-related treatment approaches.

In one embodiment, the active agent(s) for treating an Alzheimer's disorder is not IL10.

In one embodiment of the invention, the therapeutic agent effective in the treatment of an Alzheimer's disorder is donepezil and low dose IL-2.

In one embodiment of the invention, the therapeutic agent effective in the treatment of an Alzheimer's disorder is galantamine and low dose IL-2.

In one embodiment of the invention, the therapeutic agent effective in the treatment of an Alzheimer's disorder is rivastigmine and low dose IL-2.

In one embodiment of the invention, the therapeutic agent effective in the treatment of an Alzheimer's disorder is tacrine and low dose IL-2.

In one embodiment of the invention, the therapeutic agent effective in the treatment of an Alzheimer's disorder is memantine and low dose IL-2.

In another embodiment of the invention, the therapeutic agent effective in the treatment of an Alzheimer's disorder to be combined with the invention cannot be corticosteroid immunosuppressive agents.

In one embodiment of the invention, the subject is a mammal and preferably a human. In one embodiment of the invention, the subject is a female. In another embodiment of the invention, the subject is a male.

In one embodiment of the invention, the subject has been diagnosed with an Alzheimer's disorder since less than 10 years, 9, 8, 7, 6, 5, 4, 3 years, preferably less than 2 years, more preferably less than 1 year.

In one embodiment of the invention, the subject is at risk of developing a neurodegenerative disease with an Alzheimer's disorder.

Examples of risk factor to develop an Alzheimer's disorder are but not limited to: severe head trauma, diabetes, cardiovascular diseases.

In one embodiment of the invention, the subject has a familial predisposition to an Alzheimer's disorder.

In one embodiment of the invention, the subject has a genetic predisposition to an Alzheimer's disorder.

Examples of genetic predisposition for developing an Alzheimer's disorder are but not limited to: the inheritance of the ε4 allele of the apolipoprotein E (APOE), mutations in the TRPM2 (clusterin) have been associated with a 3 to 5 times higher risk of developing an Alzheimer's disorder; cytochrome P46 (which modifies cholesterol); oxidized low density lipoprotein receptor 1; angiotensin 1-converting enzyme; PICALM (phosphatidylinositol-binding clathrin assembly protein), Myc box-dependent-interacting protein 1 (BIN1); CD2-associated protein (CD2AP); CR1 (complement receptor 1); CD33; mutations and low frequency missense variants in TREM2; mutations in ephrin type-A receptor 1 (EPHA1); membrane-spanning 4-domains, subfamily A, member 4A and 6A (MS4A4A/MS4A6A); ATP-binding cassette, sub-family A (ABC1), member 7 (ABCA7); DSG2; PTK2B; SORL1; SLC24A4; RIN3; CASS4; INPP5D; NME8; MEF2C; FERMT2; ZCWPW1; TREML2; SPPL2A; ECHDC3; NDUFAF6; TRIP4; ADAMST20; SCIMP; HS3ST1; CLU; HLA-DRB5-HLA-DRB1; and CELF1.

In one embodiment of the invention, the subject has an autosomal dominant familial form of Alzheimer disease. Examples of mutations for autosomal dominant familial form of Alzheimer disease are but not limited to: mutations within amyloid precursor protein (APP), presenilins 1 and 2.

In one embodiment of the invention, the subject is affected by Down syndrome.

In one embodiment of the invention, the subject presents hippocampal or medial temporal atrophy.

In one embodiment of the invention, the subject has a Mini Mental State Examination (MMSE) inferior to 27.

In one embodiment of the invention, the cerebrospinal fluid or plasma of the subject is positive for Alzheimer's disorder diagnostic biomarkers, and/or presents abnormal values and/or abnormal ratios of said diagnostic biomarkers. These markers include but are not limited to: Aβ42 amyloid peptide, Aβ40 amyloid peptide, Tau protein, phosphorylated Tau protein, inflammatory biomarkers, oxidative stress biomarkers, biomarkers of synaptic damage and/or neurodegeneration.

The present invention also relates to a method for treating an Alzheimer's disorder in a subject in need thereof, wherein said method comprises administering to the subject a therapeutically effective amount of a Treg booster.

In one embodiment of the invention, the method for treating an Alzheimer's disorder in a subject in need thereof comprises a chronic treatment.

In another embodiment of the invention, the method for treating an Alzheimer's disorder in a subject in need thereof comprises an acute treatment.

Examples of administration include, but are not limited to:
Repeated dosing once daily for 5 to 30 days at daily dosage from 0.1 to 3.5 or 3 M IU/day.
Repeated dosing once daily for 5 to 30 days every 3 to 6 month at daily dosage from 0.1 to 3.5 or 3 M IU/day.
Repeated dosing once daily for 5 to 30 days once a year at daily dosage from 0.1 to 3.5 or 3 M IU/day.
Repeated dosing once daily for 5 to 30 days every 2, 3, 4, 5, 6, 7, 8, 9 or 10 years at daily dosage from 0.1 to 3.5 or 3 M IU/day.

In one embodiment, the treatment comprises at least a first course wherein a dose of about 0.2 $MUI/m^2$ of interleukin-2 is administered once a day during at least 1, 2, 3, 4, 5, 6, 7, 8, 9 or 10 consecutive days, followed by a maintenance dose of about 0.2 $MUI/m^2$ after one to three weeks.

In another embodiment, the treatment comprises at least a first course wherein a dose of about 0.2 $MUI/m^2$ of interleukin-2 is administered once a day from 3 to 10 consecutive days, followed by a maintenance dose of about 0.2 $MUI/m^2$ after one to three weeks.

In another embodiment, the treatment comprises at least a first course wherein a dose of about 0.2 $MUI/m^2$ of interleukin-2 is administered once a day from 5 to 10 consecutive days, followed by a maintenance dose of about 0.2 $MUI/m^2$ after one to three weeks.

In another preferred embodiment, the treatment comprises at least a first course wherein a dose of about 0.6 $MUI/m^2$ of interleukin-2 is administered once a day during at least 1, 2, 3, 4, 5, 6, 7, 8, 9 or 10 consecutive days, followed by a maintenance dose of about 0.6 $MUI/m^2$ after two to 4 weeks.

In another preferred embodiment, the treatment comprises at least a first course wherein a dose of about 0.6 $MUI/m^2$ of interleukin-2 is administered once a day from 3 to 10 consecutive days, followed by a maintenance dose of about 0.6 $MUI/m^2$ after two to 4 weeks.

In another preferred embodiment, the treatment comprises at least a first course wherein a dose of about 0.6 $MUI/m^2$ of interleukin-2 is administered once a day from 5 to 10 consecutive days, followed by a maintenance dose of about 0.6 $MUI/m^2$ after two to 4 weeks.

In another embodiment, the treatment comprises at least a first course wherein a dose of about 1.8 $MUI/m^2$ of interleukin-2 is administered once a day during at least 1, 2, 3, 4, 5, 6, 7, 8, 9 or 10 consecutive days, followed by a maintenance dose of about 1.8 $MUI/m^2$ after about one to two months.

In another embodiment, the treatment comprises at least a first course wherein a dose of about 1.8 $MUI/m^2$ of interleukin-2 is administered once a day from 3 to 10 consecutive days, followed by a maintenance dose of about 1.8 $MUI/m^2$ after about one to two months.

In another embodiment, the treatment comprises at least a first course wherein a dose of about 1.8 $MUI/m^2$ of interleukin-2 is administered once a day from 5 to 10 consecutive days, followed by a maintenance dose of about 1.8 $MUI/m^2$ after about one to two months.

In another embodiment, the treatment comprises at least a first course wherein a dose of about 0.2 $MUI/m^2$ of interleukin-2 is administered once a day during at least 1, 2, 3, 4, 5, 6, 7, 8, 9 or 10 consecutive days, followed by a maintenance dose of about 0.2 MUI/m² after one to three weeks, which maintenance dose can be repeated every one to three weeks.

In another embodiment, the treatment comprises at least a first course wherein a dose of about 0.2 MUI/m² of interleukin-2 is administered once a day from 3 to 10 consecutive days, followed by a maintenance dose of about 0.2 MUI/m² after one to three weeks, which maintenance dose can be repeated every one to three weeks.

In another embodiment, the treatment comprises at least a first course wherein a dose of about 0.2 MUI/m² of interleukin-2 is administered once a day from 5 to 10 consecutive days, followed by a maintenance dose of about 0.2 MUI/m² after one to three weeks, which maintenance dose can be repeated every one to three weeks.

In another embodiment, the treatment comprises at least a first course wherein a dose of about 0.6 MUI/m² of interleukin-2 is administered once a day during at least 1, 2, 3, 4, 5, 6, 7, 8, 9 or 10 consecutive days, followed by a maintenance dose of about 0.6 MUI/m² after 2 to 4 weeks, which maintenance dose can be repeated every 2 to 4 weeks.

In another preferred embodiment, the treatment comprises at least a first course wherein a dose of about 0.6 MUI/m² of interleukin-2 is administered once a day from 3 to 10 consecutive days, followed by a maintenance dose of about 0.6 MUI/m² after two to 4 weeks, which maintenance dose can be repeated every 2 to 4 weeks.

In another preferred embodiment, the treatment comprises at least a first course wherein a dose of about 0.6 MUI/m² of interleukin-2 is administered once a day from 5 to 10 consecutive days, followed by a maintenance dose of about 0.6 MUI/m² after two to 4 weeks, which maintenance dose can be repeated every 2 to 4 weeks.

In another embodiment, the treatment comprises at least a first course wherein a dose of about 1.8 MUI/m² of interleukin-2 is administered once a day during at least 1, 2, 3, 4, 5, 6, 7, 8, 9 or 10 consecutive days, followed by a maintenance dose of about 1.8 MUI/m² after one to two months, which maintenance dose can be repeated every one to two months.

In another embodiment, the treatment comprises at least a first course wherein a dose of about 1.8 MUI/m² of interleukin-2 is administered once a day from 3 to 10 consecutive days, followed by a maintenance dose of about 1.8 MUI/m² after about one to two months, which maintenance dose can be repeated every one to two months.

In another embodiment, the treatment comprises at least a first course wherein a dose of about 1.8 MUI/m² of interleukin-2 is administered once a day from 5 to 10 consecutive days, followed by a maintenance dose of about 1.8 MUI/m² after about one to two months, which maintenance dose can be repeated every one to two months.

According to the present invention, IL-2 may be administered at a dose of D/10 to 20×D, preferably D/5 to 10×D, wherein D is the minimal dose triggering induction of expression of CD25 in Treg, without inducing expansion of Treg.

This method for determining the appropriate low-dose of IL-2 is particularly useful when a route of administration different from the subcutaneous route is contemplated.

Especially such dosage may be useful in oral, nasal or rectal delivery.

Determination of CD25 levels can be accomplished using anti-CD25 antibodies in flow cytometry.

In this regard, lymphocyte-containing samples may be fixed with a suitable fixing agent (e.g. paraformaldehyde, which may be used at 1% in phosphate-buffered saline (PBS)) to permit the subsequent quantification or qualitative determination of the cell surface marker (e.g. by the use of flow cytometry) as convenient (e.g. following transport from the site of collection and culture of the lymphocyte-containing sample, to a flow cytometry laboratory). Commercially available Anti-CD25 monoclonal antibodies (mAbs) labeled to different fluorochrome such as Alexa488 (Molecular Probes, Oreg., USA) and FITC (Sigma) are available.

The present invention also relates to a method for preventing, reducing or alleviating the symptoms associated with an Alzheimer's disorder in a subject in need thereof, wherein said method comprises administering to the subject a therapeutically effective amount of a Treg booster.

The present invention also relates to a method for delaying the onset of an Alzheimer's disorder in a subject in need thereof, wherein said method comprises administering to the subject a therapeutically effective amount of a Treg booster.

The present invention also relates to a method for monitoring Treg cells in subjects.

The need for administering multiple cycles of IL-2 treatment can be assessed by monitoring Treg cells in subjects.

In one embodiment of the invention, it is best to reach and/or maintain the Tregs percent level between 5-10% of total T cells. In a preventive setting, it is desirable to reach and/or maintain Tregs percent level between 4.5-7% of total T cells.

In one embodiment, IL-2 doses may be adapted according to subjects' response, i.e. the effects on Tregs percentage and their boosted status (CD25$^+$ and/or Foxp3$^+$ and/or CD127$^-$ and/or PD1$^-$.

Another object of the invention is thus a method for determining whether an IL-2 treatment or dose has to be modified in a subject treated with IL-2, which method comprises monitoring the quantity of Tregs and/or CD25$^+$ and/or Foxp3$^+$ and/or CD127$^-$ and/or PD1$^-$ expression level in Tregs.

A quantity of Tregs and/or CD25$^+$ and/or Foxp3$^+$ and/or CD127$^-$ and/or PD1$^-$ expression level in Tregs inferior to the control value, means that the dose of IL-2 is to be increased. The control value is generally the baseline quantity of Tregs and/or CD25$^+$ and/or Foxp3$^+$ and/or CD127$^-$ and/or PD1$^-$ expression level in the subject, before any treatment.

In one embodiment of the invention, such quantification can be conducted when the treatment is initiated. If Tregs percentages or CD25$^+$ and/or Foxp3$^+$ and/or CD127$^-$ and/or PD1$^-$ expression levels are below a 20% increase compared to baseline, the dose of IL-2 can be increased (e.g. ×2) and the process repeated until a dose (below 3.5 MIU/day) inducing proper Treg response is found.

This method may also be conducted during the maintenance period, which involves quantifying the number of Tregs and/or the expression level of CD25$^+$ and/or Foxp3$^+$ and/or CD127$^-$ and/or PD1$^-$ in Tregs every 2 to 6 months, preferably between 1 to 5 days after administration of IL-2. If Tregs percentages and/or CD25$^+$ and/or Foxp3$^+$ and/or CD127$^-$ and/or PD1$^-$ expression levels are below a 20% increase compared to baseline, the dose of IL-2 could be increased (e.g. ×2).

EXAMPLES

The present invention is further illustrated by the following examples.

Figure 1:
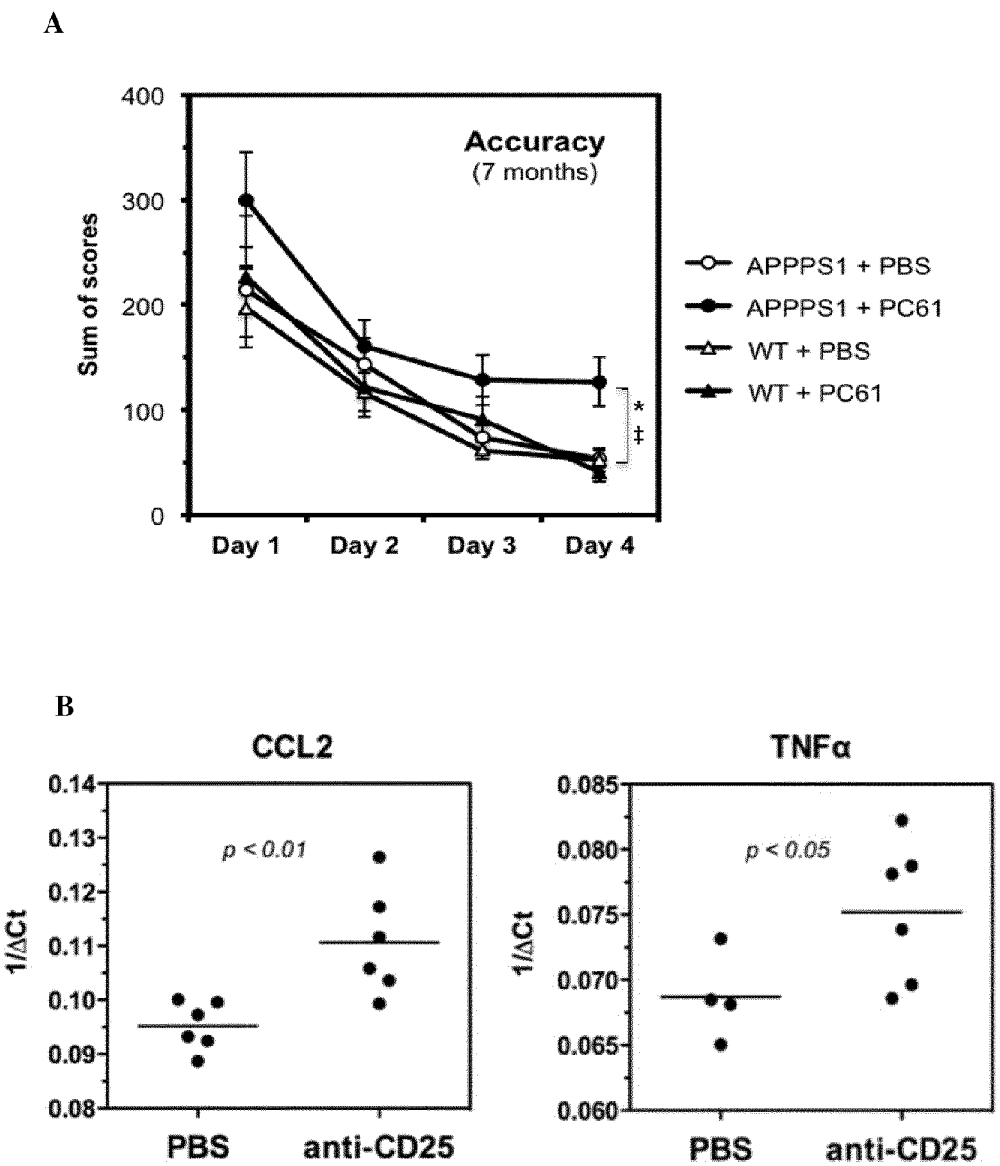
FIG. 1 represents graphs showing that transient early depletion of Treg cells accelerates the onset of cognitive deficits and enhances neuroinflammation in APPPS1 mice. (A) shows the impact of transient early Treg depletion (anti-CD25, clone PC61) on learning abilities of 7-months old APPPS1 mice, as evaluated by the Barnes maze test. (B) shows the impact of transient early Treg depletion on the expression of CCL2 and TNFα mRNA in the brain of 4-months old APPPS1 mice.

Example 1: Transient Early Depletion of Treg Cells Accelerates the Onset of Cognitive Deficits in APPPS1 Mice In order to evaluate the role of regulatory T cells (Tregs) in the pathophysiology of AD, the impact of transient Treg depletion on disease evolution was analyzed in the APPPS1 mouse model. Depletion of $CD4^+CD25^+$ Treg cells was initiated at early disease stages, i.e. before the formation of first amyloid plaques, by intraperitoneal injection of anti-CD25 depleting antibody (clone PC61) at 4-6 weeks of age, followed by a second injection 4 weeks later. The impact of Treg depletion on the onset of cognitive deficits was analyzed 5 months later, i.e. one month before the age of expected onset in untreated APPPS1. Alteration in learning and spatial memory was detected starting from 7 months of age in Treg-depleted APPPS1 mice, while PBS-treated APPPS1 animals were not yet cognitively impaired as compared to wt mice (FIG. 1A). On the graph, statistical analysis shows a significant difference between APPPS1+PC61 vs WT+PBS & WT+PC61 (*$p<0.05$); as for APPPS1+PC61 vs APPPS1+PBS (‡$p<0.05$). Early cognitive impairment in Treg-depleted mice was correlated with alterations in the neuroinflammatory response that is associated with disease progression. Treg-depleted APPPS1 mice displayed a >3 fold increase in TNFα and CCL2 mRNA expression in the brain, suggesting that Treg responses down-modulate Aβ-induced neuroinflammation in the course of AD (FIG. 1B). Altogether, these data suggest that Tregs modulate the kinetics of disease progression in AD mice by down-modulating neuroinflammation.

Figure 2:
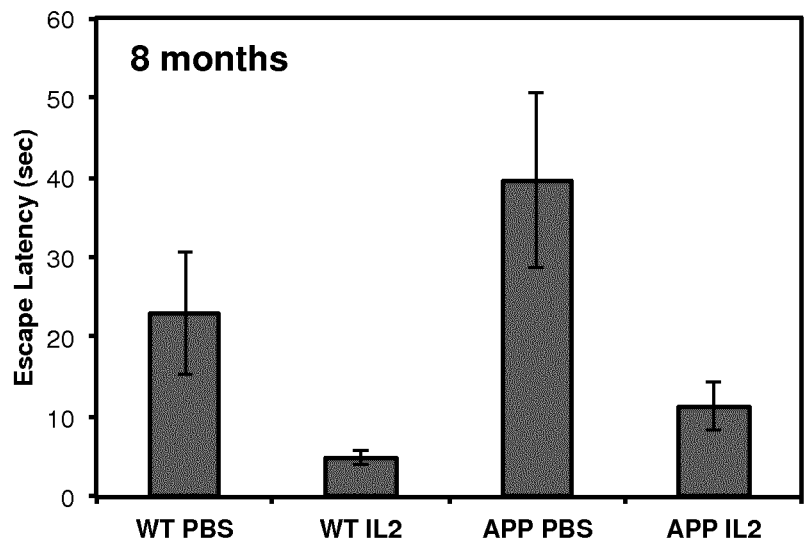
FIG. 2 represents graphs showing that early transient low-dose IL-2 treatment delays the onset of cognitive deficits in APPPS1 mice. Impact of IL-2 treatment on short-term spatial memory (probe assay) was evaluated by the Barnes maze test at 8 months (A) and 10 months of age (B).
Figure 2:
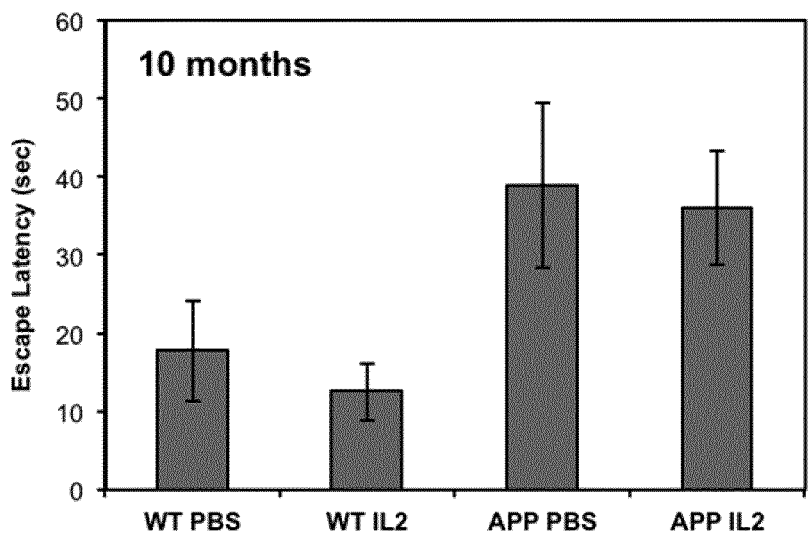

Example 2: Low-Dose IL-2 Treatment Delays the Onset of Cognitive Deficits in APPPS1 Mice Our depletion studies using the anti-CD25 antibody suggest that Treg cells play a beneficial role in the pathophysiology of AD and delay disease progression in a mouse model. The therapeutic potential in APPPS1 mice of low-dose 1-2 treatment was thus investigated. APPPS1 mice received daily intraperitoneal injections of low doses (50, 000 IU/mice/day) of recombinant IL-2 for 10 days, starting at 6 weeks of age, which correspond to the age of appearance of the first amyloid plaques in this model. The impact of low-dose IL-2 treatment on disease progression was determined by evaluating cognitive functions at the age of expected onset of cognitive deficits in untreated APPPS1 mice (8 months) and two months later. At 8 months of age, untreated APPPS1 mice display altered short-term spatial memory as compared to untreated WT animals. In contrast, 8 months-old APPPS1 mice that had been transiently treated with low doses of IL-2 at early disease stages did not show impairment in short-term memory. IL-2-treated WT mice also performed better than untreated WT animals in the short-memory assay (FIG. 2A). When short-term memory was reassessed two months later in the same animals, IL-2-treated APPPS1 mice displayed similar cognitive impairment than untreated APPPS1 mice. IL-2-treated WT animals also did not perform better than untreated WT mice at 10 months of age (FIG. 2B). These data suggest that transient low-dose IL-2 treatment at early disease stages modulates the kinetics of disease progression and delays the onset of cognitive deficits.

Figure 3A:
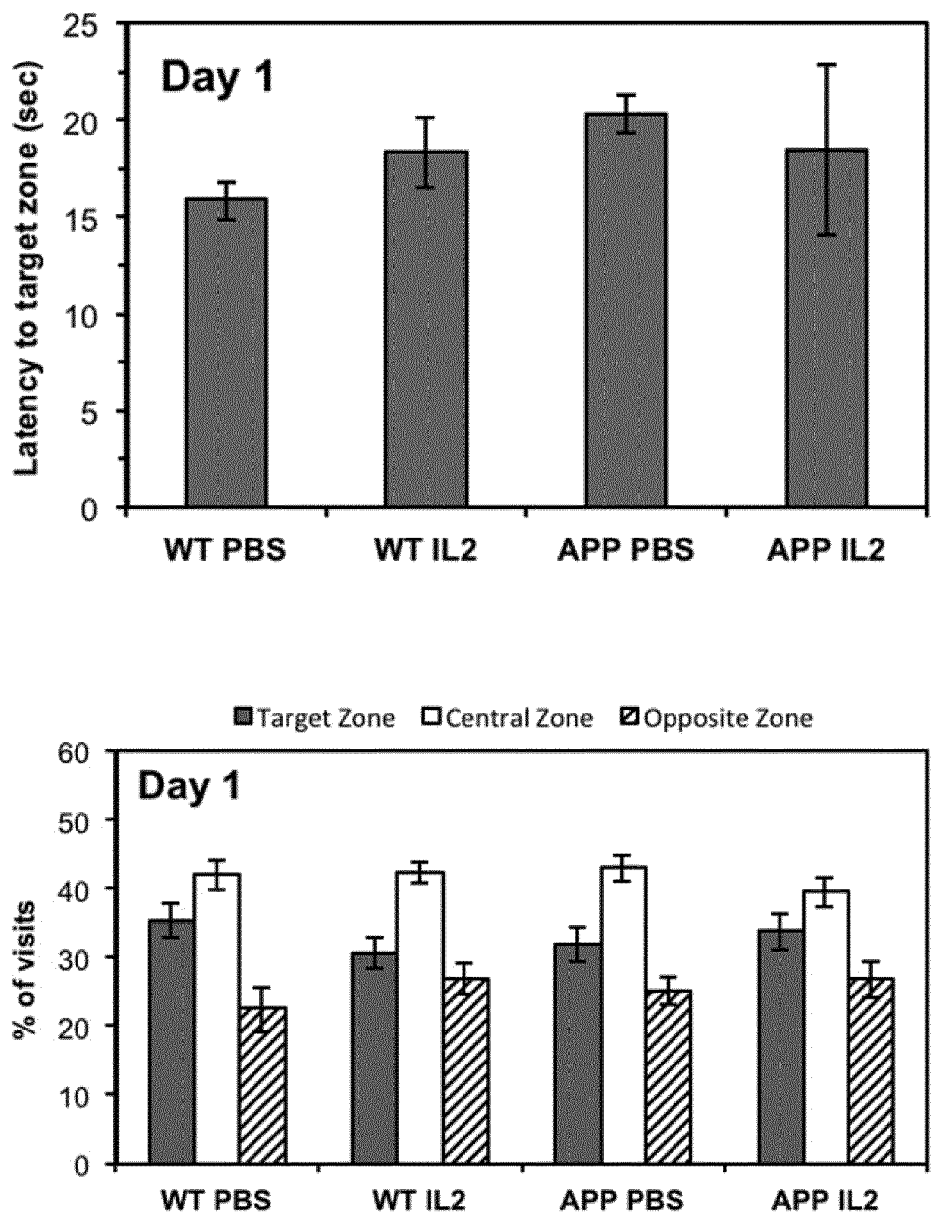
FIG. 3 represents graphs showing that early transient low-dose IL-2 treatment improves learning abilities and cognitive behavior of APPPS1 mice at later disease stages. 6 weeks-old APPPS1 mice were injected daily i.p. with either PBS or 50,000 IU of rhIL-2 for 10 days. (A, B) show the impact of IL-2 treatment on learning capacities of APPPS1 mice at later disease stages (10 months) was evaluated by the Barnes maze test. Results on the first (A) and last day (B) of the learning phase are depicted. (C) shows the impact of IL-2 treatment on spontaneous alternation in the Y maze test (initial exploration phase). (D) shows the impact of IL-2 treatment on the secondary recall exploration phase of the Y maze test. Mean+/−s.e.m (n=10-11 mice/group) (*$p<0.05$; **$p<0.01$).
Figure 3B:
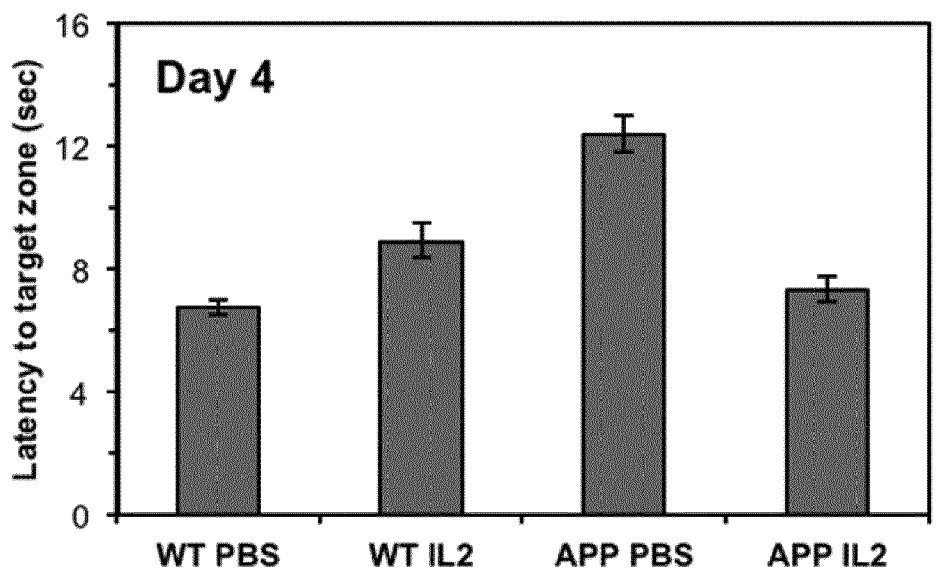
Figure 3B:
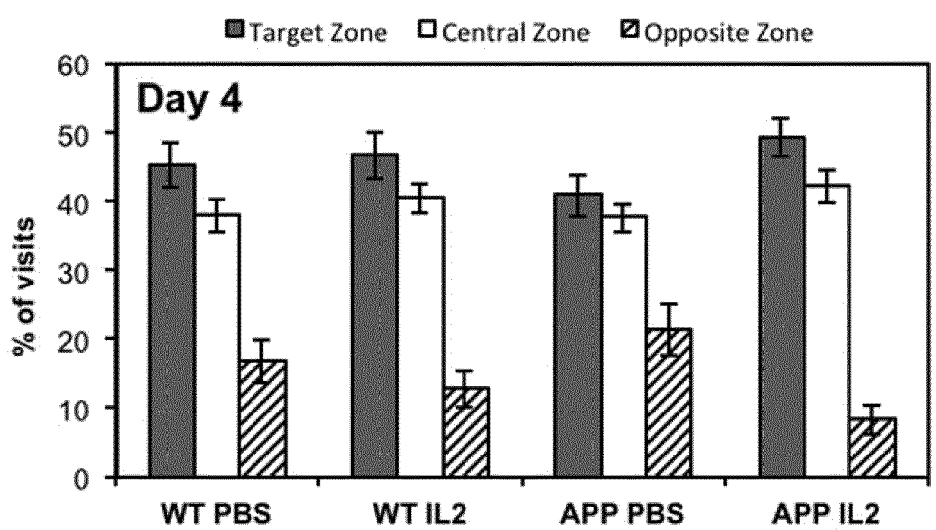

To further investigate if cognitive improvement could still be detected in IL-2-treated mice at 10 months of age, additional analyses were carried out for better evaluating the exploration strategy of mice during the learning phase of the behavior test, as described in Material and Methods. The platform area was divided in three longitudinal parts of equal width and the latency to reach the target zone as well as the numbers of visits to each zone were quantified. At day 1 of the learning phase, as expected, visit latency to target zone was slightly higher for untreated APPPS1 than WT mice, but no difference was detected between IL-2-treated and untreated APPPS1 animals (FIG. 3A, upper panel). In contrast, after 4 days of learning, whereas untreated APPPS1 mice spent twice more time than untreated WT animals to reach the target zone, the latency to target zone was similar for IL-2-treated APPPS1 and untreated WT mice (FIG. 3B, upper panel). In the same line, the percentage of visits to each zone of the platform area was relatively similar within each group of mice at day 1, with a preference for the central starting zone (FIG. 3A, lower panel). However, after completion of the learning phase (day 4), IL-2-treated APPPS1 mice displayed reduced percentage of visits to the opposite zone and increased frequency of visits to the target zone as compared to untreated APPPS1 animals (FIG. 3B, lower panel). These data indicate that improved learning abilities still persist at later disease stages in APPPS1 mice following early transient low-dose IL-2 treatment.

Figure 3C:
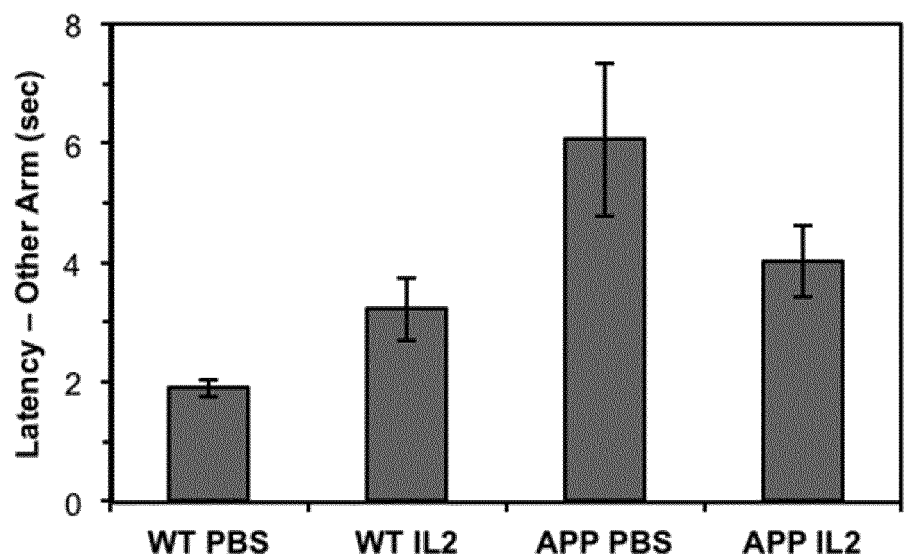
Figure 3C:
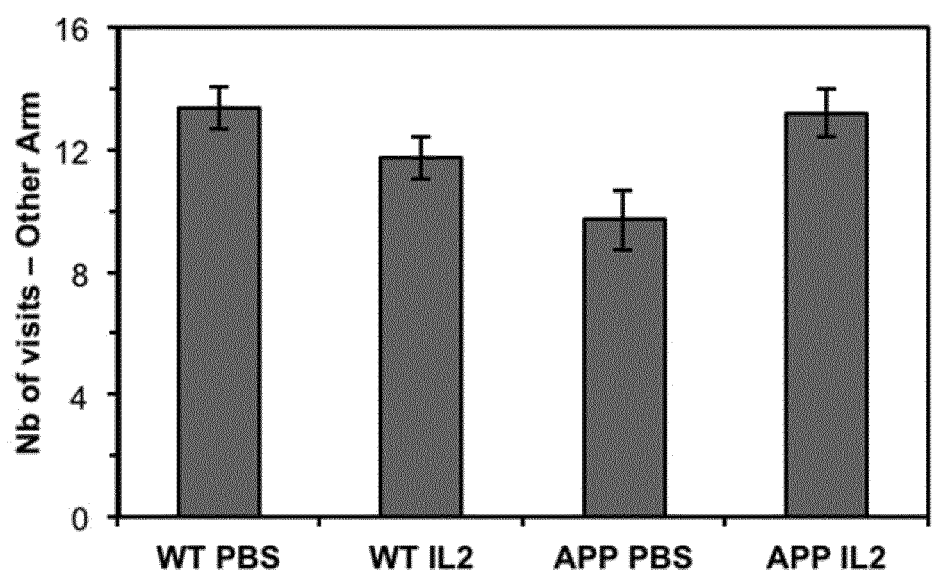
Figure 3D:
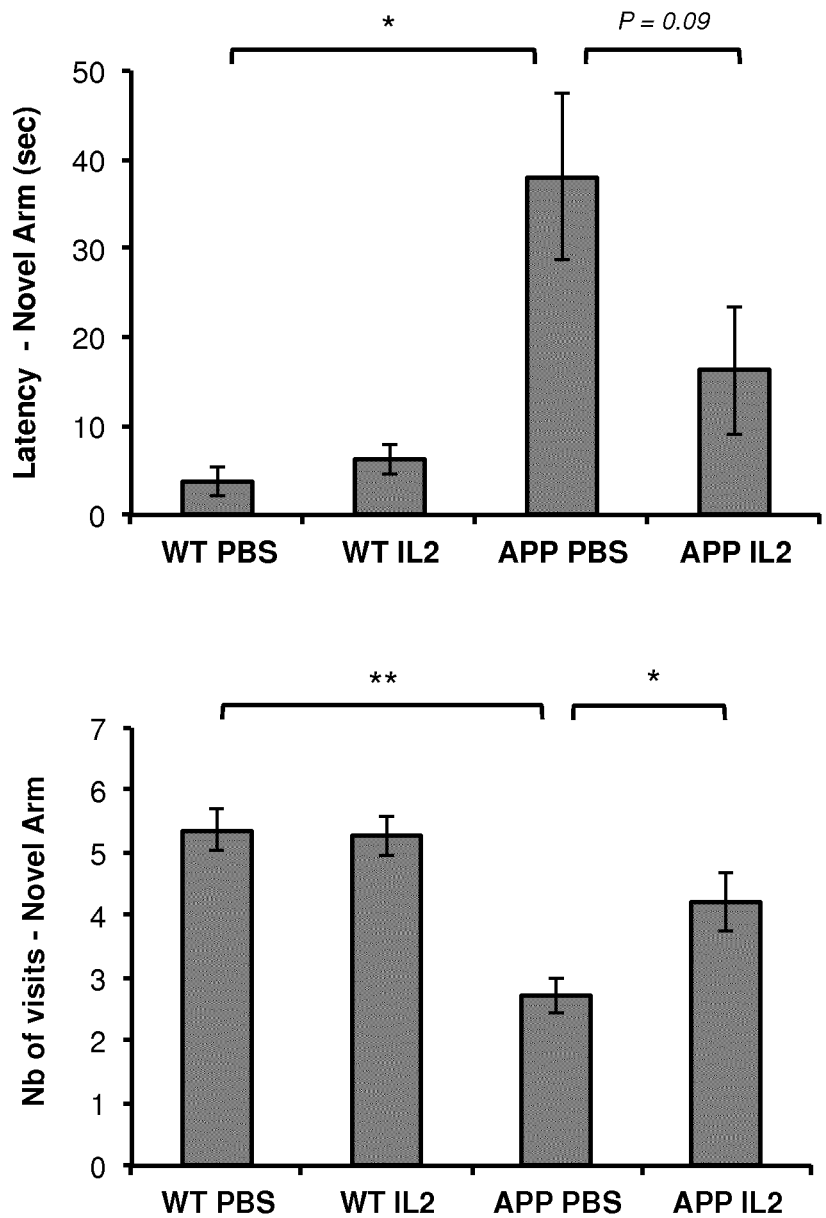

The impact of IL-2 treatment on cognitive behavior at later disease stages was also analyzed by evaluating spontaneous alternation in the Y maze test. Whereas the latency to visit non-starting arm was higher for untreated APPPS1 than WT mice during the initial exploration phase, latency was reduced in IL-2-treated APPPS1 as compared to untreated APPPS1 (FIG. 3C, upper panel). Similarly, the total number of visits to the non-starting arm was lower in untreated APPPS1 than WT mice, whereas number of visits was similar in IL-2-treated APPPS1 and untreated WT mice (FIG. 3C, lower panel). Similar beneficial effects of transient low-dose IL-2 treatment were also observed during the secondary recall exploration phase of the Y maze test. As compared to WT mice, untreated APPPS1 animal display significantly higher latency and reduced number of visits to the novel arm. In contrast, IL-2-treated APPPS1 mice show a tendency (p=0.09) towards reduced latency to visit the novel arm (FIG. 3D, upper panel), and significantly higher number of visits to the novel arm (FIG. 3D, lower panel) than untreated APPPS1 animals. These data confirm that early transient IL-2 treatment results in improved cognitive behavior at later disease stages in APPPS1 mice.

Figure 4:
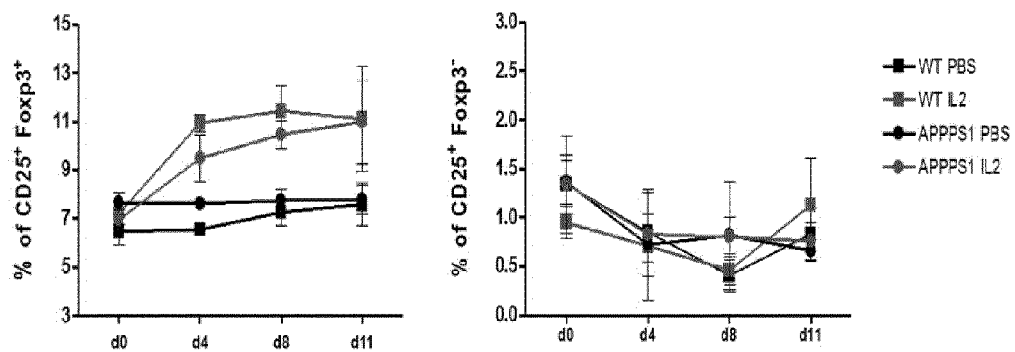
FIG. 4 represents graphs showing that low-dose IL-2 treatment specifically amplifies Treg cells in APPPS1 mice. Six weeks-old WT and APPPS1 mice were injected daily i.p. with either PBS or 50,000 IU of rhIL-2 for 10 days. Flow cytometry analysis was carried out to determine the percentage of Treg cells ($CD25^+Foxp3^+$) and Teff cells ($CD25^+Foxp3^-$) among the $TCR\beta^+CD4^+$ population, (A) in the blood (before injection, and on day 4, 8 and 11) and (B) in the spleen and pooled lymph nodes the day after treatment completion (day 11). Mean+/−SD (3-4 mice/group).
Figure 4:
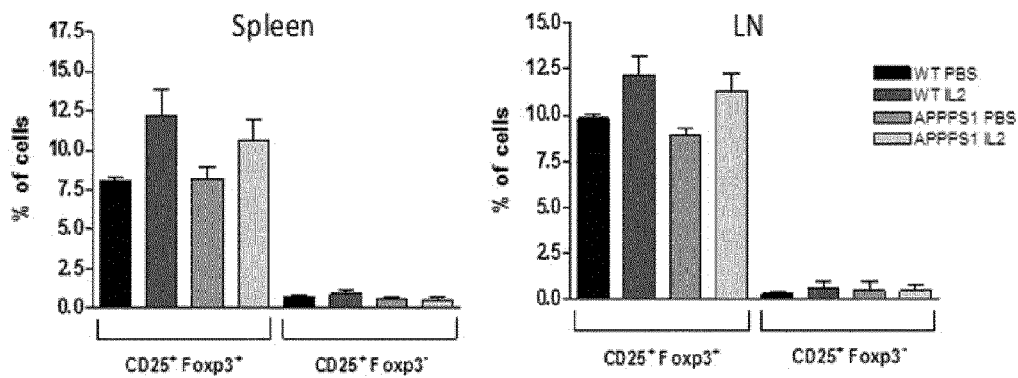

Example 3: Low-Dose IL-2 Treatment Selectively Enhances Treg Cells in WT and APPPS1 Mice Pilot experiments were first carried out to evaluate the impact of low-dose IL-2 treatment on the frequency of Treg cells in WT and APPPS1 mice. Animals received daily intraperitoneal injections of either PBS or low doses (50,000 IU/mice/day) of recombinant IL-2 for 10 days, starting at 6 weeks of age, i.e. the age of appearance of the first amyloid plaques in this model. Frequency of both $CD4^+CD25^+Foxp3^+$ Tregs and $CD4^+CD25^+Foxp3^-$ effector T cells (Teff) was monitored in the blood, before treatment and 4, 8 or 11 days after the first injection. Tregs and Teff frequencies in the spleen and pooled lymph nodes were also analyzed the day after completing the treatment (day 11). Flow cytometry analyses showed that Treg frequency was significantly enhanced in the blood of both WT and APPPS1 mice, as soon as after 4 days of low-dose IL-2 administration (FIG. 4A, left panel). A similar increase in Tregs was still observed in both the spleen and lymph nodes the day after treatment completion (FIG. 4B). In contrast, low-dose IL-2 treatment did not significantly alter the frequency of Teff, neither in the blood, spleen, nor lymph nodes (FIGS. 4A, right panel and 4B). Of note, no difference in the percentages of $CD8^+$ T cells and $CD19^+$ B cells was observed in IL-2-treated mice (data not shown). These data confirmed that low-dose IL-2 treatment selectively enhances the frequency of Tregs in both WT and APPPS1 mice, without significantly amplifying neither $CD4^+$ effector T cells nor other immune effectors.

Figure 5A:
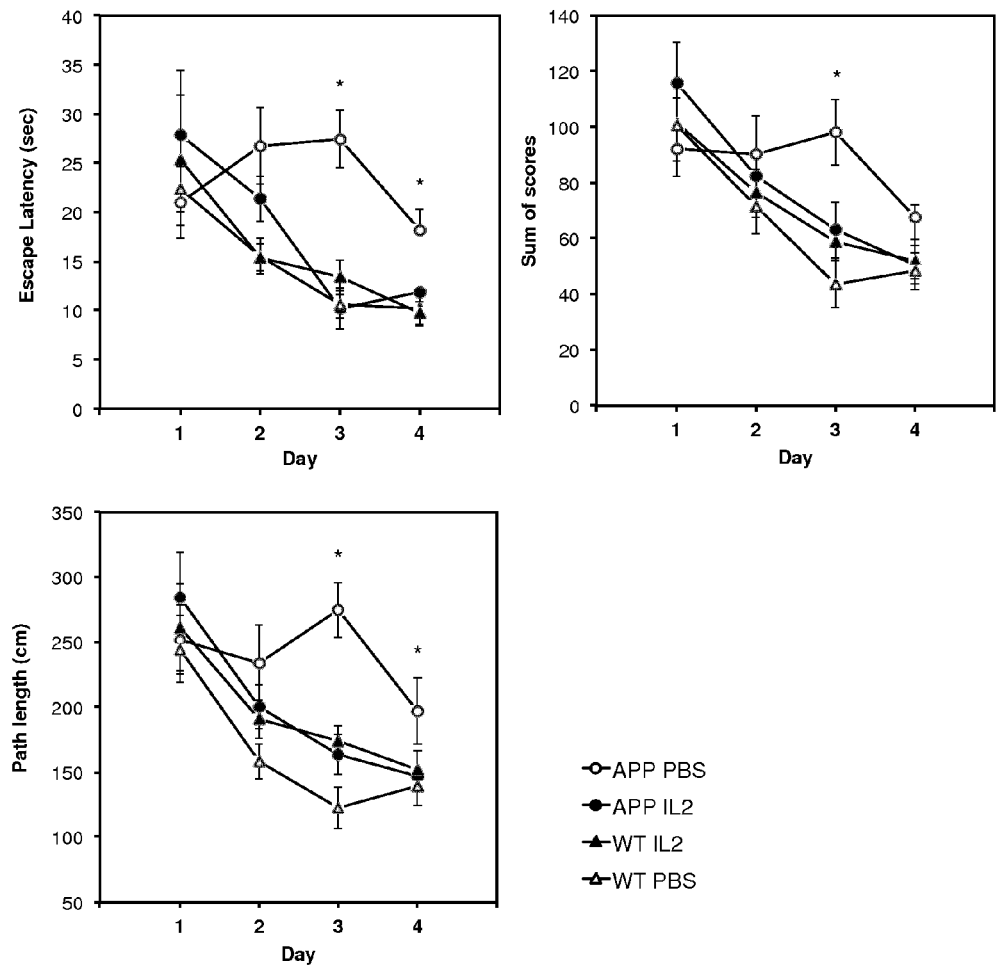
FIG. 5 represents graphs showing that sustained low-dose IL-2 treatment better improves cognitive functions in APPPS1 mice at later disease stages. Six weeks-old WT and APPPS1 mice were injected daily i.p. with either PBS or 50,000 IU of rhIL-2 for 10 days, followed by subsequent additional daily injections of low-doses of IL-2 for 5 days every 3 weeks. Impact of sustained low-dose IL-2 treatment on learning capacities of APPPS1 mice at later disease stages (10 months) was evaluated by Barnes maze (A) and Y maze test (B). Mean+/−s.e.m (n=10-11 mice/group) (*$p<0.05$).

Example 4: Sustained Low-Dose IL-2 Treatment Better Improves Cognitive Function in APPPS1 Mice at Later Disease Stages We evaluated the impact on cognitive functions of sustained, instead of transient, low-dose IL-2 administration. In addition to the initial 10 days of treatment, mice received additional daily injections of low-doses of IL-2 for 5 days every 3 weeks. Impact on learning abilities at later disease stages was evaluated by Barnes maze. At 10 months of age, PBS-treated APPPS1 mice display altered capacities in the learning phase of Barnes maze test, as evidenced by increased escape latency, increased path length, and reduced accuracy (sum of scores) as compared to untreated WT animals. Sustained low-dose IL-2 treatment significantly improved cognitive functions in 10-months old APPPS1 mice, leading to similar learning capacities than WT mice (FIG. 5A).

Of note, such improvement during the learning phase of Barnes maze was more evident after sustained IL-2 treatment than in transiently treated mice. Indeed, for these latter a beneficial effect at 10 months of age was only detected after additional analyses of the exploration strategy (cf. FIG. 3A-B).

Figure 5B:
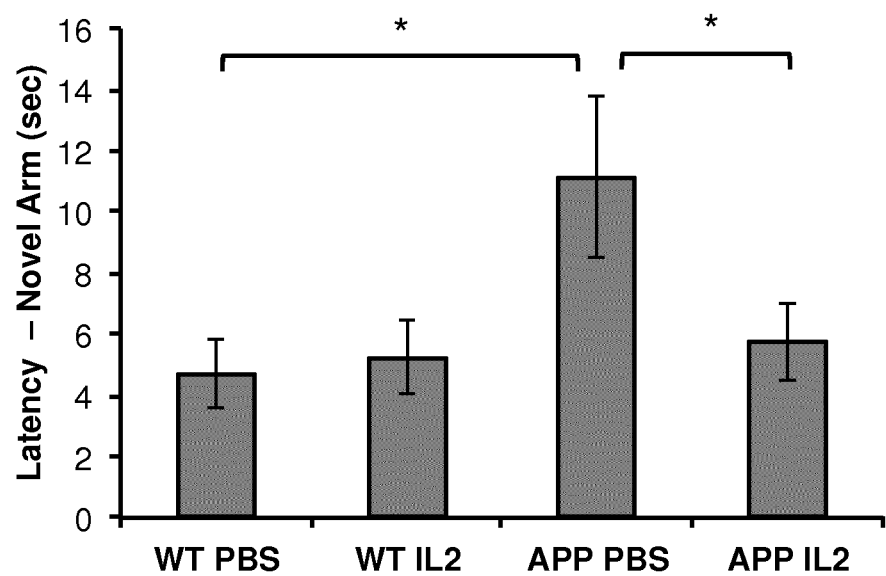

A beneficial impact of sustained IL-2 treatment was also supported by Y maze test performed at 10 months of age. Whereas PBS-treated APPPS1 mice displayed significantly higher latency than WT mice to visit the novel arm (secondary recall exploration phase), administration of sustained IL-2 treatment to APPPS1 animals restored latency similar to WT mice (FIG. 5B).

Altogether, these data suggest that sustained rather than transient low-dose IL-2 treatment may be more efficient at improving cognitive functions at later disease stages in APPPS1 mice.

Example 5: Low-Dose IL-2 Treatment Enhances Plague-Associated Microglia

Figure 6:
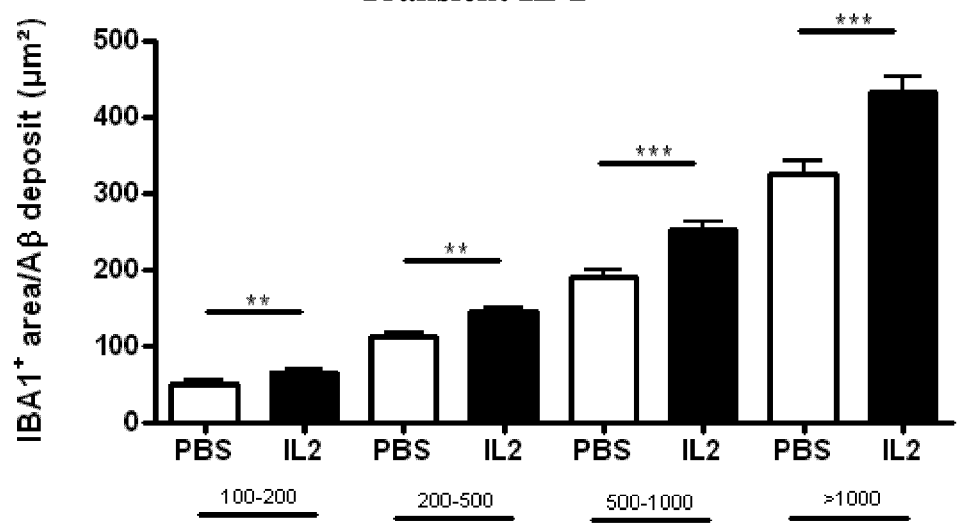
FIG. 6 represents graphs showing that low-dose IL-2 treatment enhances plaque-associated microglia. Six weeks-old WT and APPPS1 mice were injected daily i.p. with either PBS or 50,000 IU of rhIL-2 for 10 days, then left untreated (A) or subsequently injected with additional low-doses of IL-2 for 5 days every 3 weeks (B). Brains were harvested at 4 months of age and processed for immunohistochemistry studies. Recruitment of microglia towards amyloid plaques was evaluated by quantifying IBA1 staining in close proximity of or colocalizing with Aβ deposits of different size ranges (100-200; 200-500; 500-1000; >1000 μm2). Mean+/−s.e.m (n>90 plaques for each size category; from 4-6 mice/group). (*$p<0.05$; $p<0.01$; *$p<0.001$).
Figure 6:
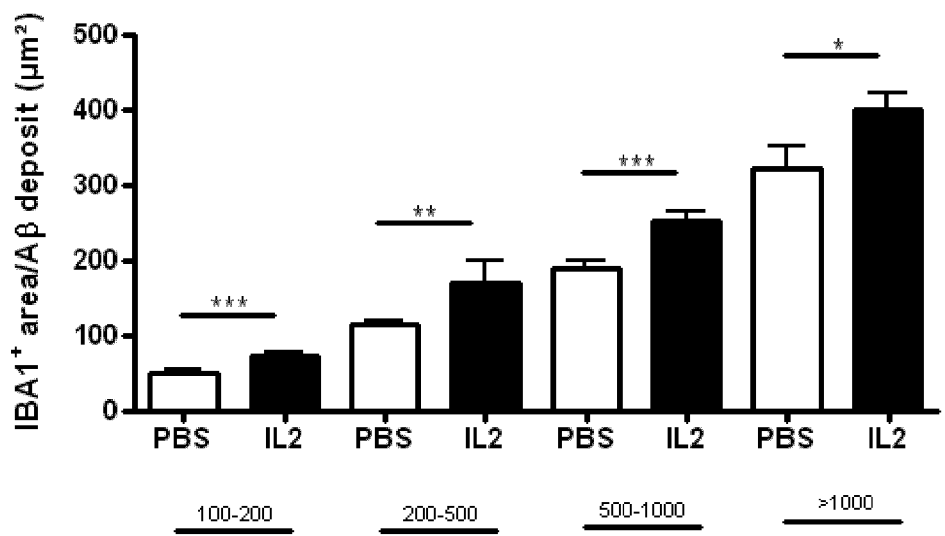

We then investigated the impact of low-dose IL-2 administration on the recruitment of microglia towards amyloid plaques. Starting at 6 weeks of age, WT and APPPS1 mice were treated for 10 days with daily injection of either PBS or low-dose IL-2 (50,000 IU/mice/day). Brains were then harvested at 4 months of age for immunohistochemistry studies. Analysis of microglia recruitment to amyloid plaques indicated that transient low-dose IL-2 treatment resulted in a significant increase in plaque-associated IBA1, for all size ranges (100-200, 200-500, 500-1000 and >1000 $\mu m^2$) of Aβ deposits (FIG. 6A). Similar results were obtained when mice received sustained instead of transient low-dose IL-2 treatment (FIG. 6B). Altogether, these data suggest that the improvement of cognitive functions observed upon low-dose IL-2 treatment was correlated with enhanced microglia recruitment towards amyloid plaques at mid-disease stages.

Figure 7:
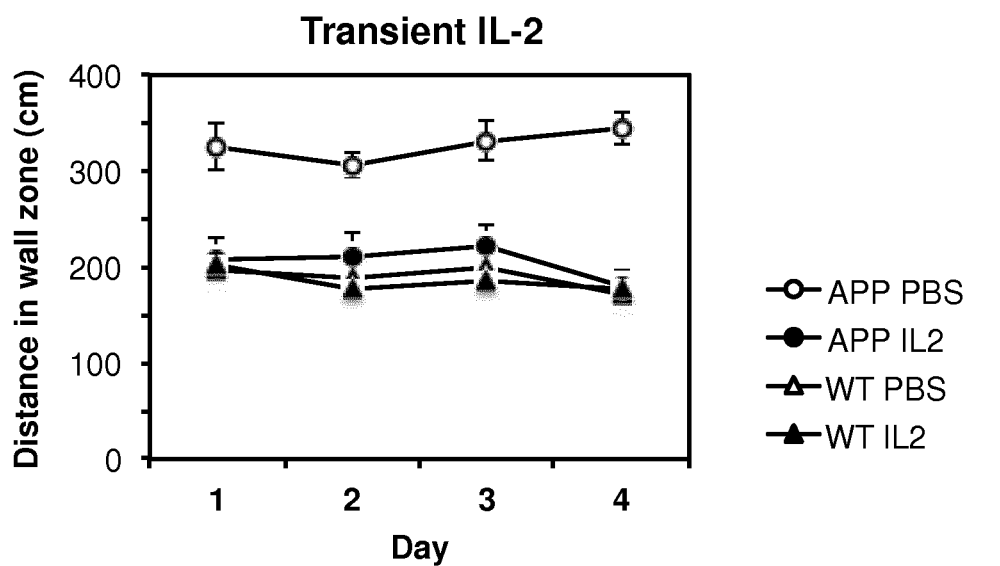
FIG. 7 represents graphs showing that low-dose IL-2 treatment reduces non-cognitive neurobehavioral disturbances at early disease stages in APPPS1 mice. Six weeks-old WT and APPPS1 mice were injected daily i.p. with either PBS or 50,000 IU of rhIL-2 for 10 days, then left untreated (Transient IL-2; upper panel) or subsequently injected with additional low-doses of IL-2 for 5 days every 3 weeks (Sustained IL-2; lower panel). Impact of IL 2 treatment on neurobehavioral disturbances at early disease stages in APPPS1 mice was evaluated at 5 months of age by the Open Field test. Mean+/−s.e.m (n=10-11 mice/group).
Figure 7:
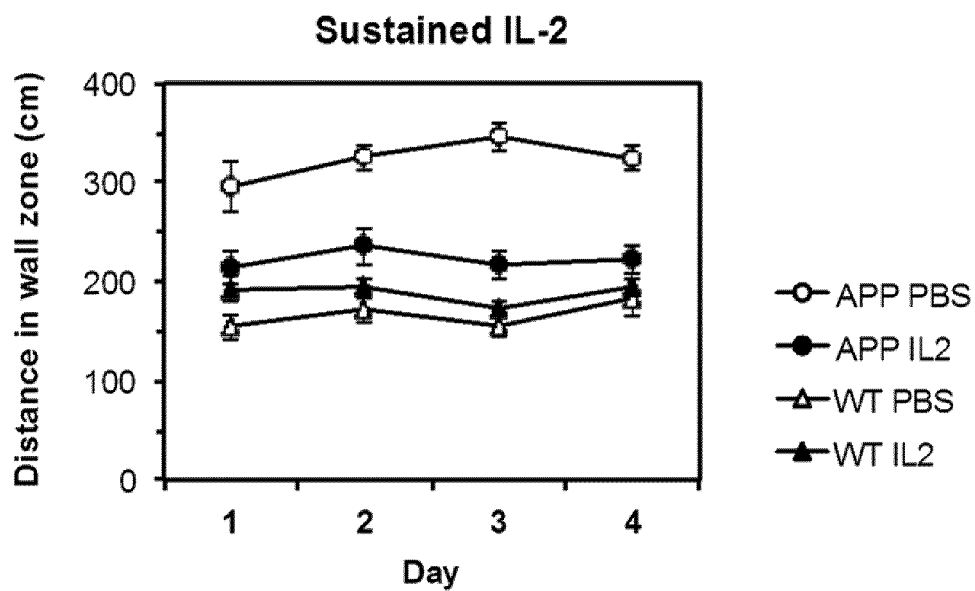

Example 6: Low-Dose IL-2 Treatment Reduces Early Disease-Related Non-Cognitive Neurobehavioral Disturbances in APPPS1 Mice The impact of either transient or sustained low-dose IL-2 treatment on non-cognitive behavioral deficits associated with early disease progression was evaluated at 5 months of age by the Open Field test. Six weeks-old WT and APPPS1 mice were injected daily i.p. with either PBS or 50,000 IU of rhIL-2 for 10 days, then left untreated or subsequently injected with additional low-doses of IL-2 for 5 days every 3 weeks. Behavior analyses indicated that untreated APPPS1 mice display increased path length in wall zones as compared to WT animals, suggesting disease-related non-cognitive behavioral alterations such as anxiety and/or disregulated locomotor activity. In contrast, APPPS1 mice treated with either transient or sustained low-dose IL-2 regimens showed a normalized phenotype with reduced path length in wall zones, similar to treated and untreated WT mice (FIG. 7). These data suggest that low-dose IL-2 treatment reduces non-cognitive neurobehavioral deficits associated with early disease progression in APPPS1 mice.

Altogether, these studies suggest that Treg cells play a beneficial role in the pathophysiology of AD, and that boosting Treg responses through low-dose IL-2 treatment starting at early disease stages delays disease progression and onset of both cognitive and non-cognitive disease-related behavior deficits in a mouse model of AD.

Materials and Methods
Material
Mice

C57BL/6j mice were purchased from Elevage Janvier (Le Genest Saint Isle, France). APPPS1 transgenic mice (Thy1-APP$^{KM670/671NL}$; Thy1-PS1$^{L166P}$) on the C57BL/6 background (Radde et al., EMBO, 2006) were kindly provided by Prof. Mathias Jucker (Hertie Institute for Clinical Brain Research, University of Tübingen, Tübingen, Germany) and maintained heterozygously by breading with wild type C57BL/6j mice. All animals were bred and maintained under strictly monitored specific and opportunistic pathogen-free conditions. All experimental protocols have been approved by the Charles Darwin ethical committee of University Pierre & Marie Curie, and were carried out in compliance with European legislation on animal care, housing and scientific experimentation.

Methods
Anti-CD25 Treatment

Four- to six-week old APPPS1 mice or wild type littermates were injected intraperitoneally with either PBS or 150-200 μg of ascite-derived anti-CD25 depleting monoclonal antibody (clone PC61) diluted in PBS. Similar treatment with PBS or anti-CD25 was repeated four weeks after the first injection. Depletion efficiency was assessed by quantifying regulatory T cells in blood samples five days following each round of injection, by a combination of intracellular and surface staining using PE-conjugated anti-Foxp3 (eBioscience, San Diego, Calif., USA), FITC-conjugated anti-CD4 (BD Biosciences, Franklin Lakes, N.J., USA), and biotinylated anti-CD25 (clone 7D4; BD Biosciences) followed by APC-conjugated streptavidin (BD Biosciences). Fluorescence data were collected on a LSRII flow cytometer (BD Biosciences) and analyzed using Flowjo software (Tree Star, Inc., Ashland, Oreg., USA). The depletion of CD4$^+$CD25$^+$ Treg cells was then initiated to determine its impact on cognitive deficit in APPPS1 mice as described in Example 1.

IL-2 Treatment

Six-week old APPPS1 mice or wild type littermates were treated daily for 10 consecutive days with intraperitoneal injections of either PBS or 50,000 IU of recombinant human IL-2 (Proleukin; Novartis, Basel, Switzerland) diluted in PBS. The impact of this treatment on on cognitive deficit in APPPS1 mice is described in Example 2. We also evaluated the impact of sustained IL-2 treatment, which consisted in additional daily low-dose IL-2 injection for 5 days every 3 weeks.

qRT-PCR Analysis

Brains from PBS- or anti-CD25-treated animals were harvested 4 weeks after the last injection and mRNA was extracted from total hemibrains. cDNA was synthesized and used as template for analyzing the expression level of 48 target genes, using custom-made RT$^2$ PCR arrays from SABiosciences (Frederik, Md., USA). Expression level relative to hprt housekeeping gene was determined using the ΔCt method in Example 1.

Flow Cytometry Analysis

The efficiency of IL-2 treatment for Treg amplification was monitored by flow cytometry using a combination of surface and intracellular staining. In a pilot cohort, Treg cells were quantified in the blood, spleen and/or lymph nodes the day before the first injection, and then at days 4, 8 and 11. Cells were first incubated with Fc receptor blocking antibody (2.4G2, BD Biosciences, Franklin Lakes, N.J., USA) to avoid non-specific staining. PE-Cy5-conjugated anti-TCRβ (H57-597), FITC-conjugated anti-CD4 (L3T4), biotinylated anti-CD25 (7D4) and APC-conjugated streptavidin (all from BD Biosciences) were used for cell-surface staining. For intranuclear staining, cells were then fixed, permeabilized and incubated with PE-conjugated anti-Foxp3 (FJK-16s, eBioscience, San Diego, Calif., USA) according to the manufacturer's protocol. Fluorescence data were collected on a LSRII flow cytometer (BD Biosciences) and analyzed using Flowjo software (Tree Star, Inc., Ashland, Oreg., USA).

Immunohistochemistry

Mice were anesthetized with a mixture of ketamine (Imalgene) and xylazine (Rompun) in 0.9% NaCl solution, then transcardially perfused with ice-cold PBS followed by a solution of 4% paraformaldehyde in PBS. The brain was harvested, transferred for 48 h at 4° C. in a fresh solution of 4% paraformaldehyde in PBS, and then transferred overnight at 4° C. in 30% sucrose/PBS solution. After bisecting across the midline, each hemi-brain was divided into anterior, median and posterior parts by coronal sectioning. Each part was then embedded individually in Optimal Cutting Temperature (OCT; WVR, Belgium) mounting medium, frozen in liquid nitrogen and stored at −80° C. 7 μm cryosections were prepared from median parts of the brain, using a Leica RM2145 cryostat, and mounted on SuperFrost Plus glass slides. At least three nonadjacent sections (100 μm apart) were analyzed for each mouse. For labeling of microglia (IBA1) and Aβ deposits, sections were first rinsed in PBS, blocked with PBS-5% BSA-0.05% Tween 20 for 1 h at room temperature, and then incubated overnight at 4° C. with rabbit anti IBA1 antibody (1/200) (Wako, Osaka, Japan) diluted in PBS-0.1% BSA. Following three washes in PBS-0.1% BSA, sections were then incubated for 30 minutes at room temperature with mouse anti-Aβ monoclonal antibody (1/200) (BAM10; Thermo Scientific, Rockford, USA) diluted in PBS-0.1% BSA. Sections were then washed three times and incubated for 30 minutes at room temperature with Alexa488-conjugated goat anti-rabbit and Alexa594-conjugated goat anti-mouse antibodies (1/1000 each) (Life Technologies, Saint Aubin, France) diluted in PBS-0.1% BSA. After three additional washes, brain sections were stained with Dapi (1 μg/ml in PBS) and coverslipped with Immu-Mount medium (ThermoShandon, Runcom, UK).

Microscopy and Image Analysis

For each mouse, three nonadjacent sections were imaged using an Olympus BX61 microscope equipped with an Olympus DP71 camera. Four random images of the cortex plus one image for the hippocampus were collected at ×20 magnification for each section. All sections were immunostained and imaged using the same parameters. Quantification of microglia recruitment around amyloid plaques was carried out by post-processing images with the ImageJ software (available from the National Institutes of Health website), after standardized binarization of fluorescence images. We first delineated the proximal surrounding area for each Aβ deposit, which was defined as the limit encompassing twice the radius of the deposit. The amount of IBA1 staining within this area, i.e. corresponding to microglia colocalizing with or in close proximity to Aβ deposit, was determined from the binarized images. Pooled data from 4-6 mice/group were analyzed, corresponding to at least n>90 deposits of each size category.

Barnes Maze

The Barnes maze is a spatial memory task based on the natural tendency of mice to escape from a bright open surface, to a dark closed environment. The maze consists of an elevated flat circular platform harboring twenty circular holes located equidistantly at the periphery of the platform. A hidden box located under one hole allows the mice to escape from the platform, and fixed visual references are displayed around the maze for mice orientation. The test consisted in 4 days of learning, followed by 1 probe assay on day 5 in which the escape box was removed. Each mouse was given four trials per day during the learning phase and a single trial for the probe test. For each trial, mice were placed in an opaque start box located in the center of the maze, ensuring a random starting orientation for each trial. After being released from the start box, mice were allowed to freely explore the maze for a maximum of 300 seconds (learning phase) or 90 seconds (probe test). Loud strident noise was used as a reinforcement to motivate the mice to escape the maze. The trial was stopped once the mouse found the escape hole or when the maximum duration of the trial was reached. When mouse did not find the escape box within 300 seconds of a learning trial, it was gently picked up and placed over the target hole, into the escape box. Mice were left in the escape box for 2 minutes before being returned to their home cage. The platform surface was carefully cleaned with 70% EtOH between each trial to remove any olfactory cues. An overhead video camera and an automated video tracking software (Viewer³ BIOBSERVE, St-Augustin, Germany) were used for recording and analyzing each behavior trial. Numbers of errors, path length and escape latency to reach the target hole were monitored. Accuracy was calculated as the sum of scores assigned to each hole visited by the mouse, with a score of 0 being assigned to target hole, 1 to adjacent holes, and so forth towards the opposite hole, which was assigned the highest score of 10. Additional analyses were carried out for further analyzing the exploration strategy of mice, by subdividing the platform area in three longitudinal parts of equal width (central zone, target zone, opposite zone) and monitoring the number of visits to each zone and the latency to reach the target zone in Example 2.

Y Maze

The Y maze test is based on the tendency of rodents not to explore previously explored areas, and has been suggested to measure several aspects of spatial working memory. The maze was made of three transparent plastic arms, 39×8×16 cm each, set at 120° angle relative to each other. The Y maze spontaneous alternation test was composed of an initial exploration phase (5 min), a retention phase out of the maze (2 min) and a secondary recall exploration phase (2 min). "Start arm" (at the extremity of which the mouse is placed at the beginning of the experiment), "Other arm" (accessible during the whole experiment), and "Novel arm" (blocked by a sliding door during the initial exploration phase and unblocked during secondary exploration) were randomly chosen for each mouse to avoid any preference-related bias. The maze was carefully cleaned with 70% EtOH between each exploration phase to remove any olfactory cues. Without prior habituation, mice were placed at the extremity of the "Start arm" and allowed to explore both the "Start arm" and "Other arm" for 5 minutes, while the "Novel arm" was blocked. After the 2 min retention phase, the "Novel arm" was unblocked and the mouse was placed back at the extremity of the "Start arm". Mice were then allowed to freely explore the three arms for 2 minutes. An overhead video camera and an automated video tracking software (Viewer³ BIOBSERVE, St-Augustin, Germany) were used for recording and analyzing each exploration phase. Number of visits, % of visits, and latency to reach "Other arm" and "Novel arm" were monitored.

Open Field

The open field Test was used for evaluating non-cognitive behavioral disturbances. On the first day, mice were placed with all their cagemates in the 33 cm×33 cm open field arena, and were allowed to freely explore their environment for 10 minutes, as an habituation step. The next four days, each mouse was placed individually in the center of the arena once a day for 10 minutes, and animal behavior was monitored. The arena was virtually divided into a central square area, corridors along each walls, and four corner squares that partly overlapped with the corridors areas. Behavioral parameters (latency, number of visits, duration, and distance) were measured for each area, using the Viewer3 BIOBSERVE Tracking System. Time and/or distance spent in the center square of the arena is considered to be an inverse measure of anxiety, since mice have a natural tendency towards the periphery where they are safer from danger.

Statistical Analysis

The results are expressed as means+/−s.e.m (errors bars) and n=10-11 mice per group. For statistical comparison of data ANOVA tests were performed.

The invention claimed is:

1. A method for treating an Alzheimer's disorder in a subject in need thereof comprising administering a therapeutically effective amount of a booster of Treg cells, wherein the booster of Treg cells is a low dose of IL-2, wherein a low dose of IL-2 is at a range below 3.5 MIU/m²/day, and wherein the subject is at an early stage of Alzheimer's disorder.

2. The method according to claim 1, wherein the low dose of IL-2 is administered to the subject prior to, concurrent to, or subsequent to other active agent(s) for treating an Alzheimer's disorder and/or side effects of said active agent(s).

3. The method according to claim 1, wherein the low dose of IL-2 is administered to the subject in need thereof by subcutaneous, intramuscular, intravenous, intraocular, transdermal, topical, parenteral, rectal, intranasal or oral administration.

4. The method according to claim 1, wherein the subject is diagnosed with an Alzheimer's disorder.

5. The method according to claim 1, wherein the subject has a genetic mutation associated with an Alzheimer's disorder.

6. The method according to claim 1, wherein the subject is affected with or has been diagnosed with an early-onset variant of an Alzheimer's disorder.

7. The method according to claim 1, wherein the low dose of IL-2 is at a range of 0.05 to 2 MIU/m$^2$/day.

8. The method according to claim 1, wherein the low dose of IL-2 is at a range of 0.2 to 1 MIU/m$^2$/day.

9. The method according to claim 1, wherein the low dose of IL-2 is administered in a sustained-release form.

10. The method according to claim 2, wherein the other active agent(s) for treating an Alzheimer's disorder are selected from the group consisting of a cholinesterase inhibitor, a N-methyl D-aspartate antagonist, a BACE1 inhibitor, a γ secretase inhibitor, passive anti-Aβ immunotherapy in the form of monoclonal anti-Aβ antibodies, active anti-Aβ immunotherapy, non-steroidal anti-inflammatory drugs, passive anti-Tau immunotherapy in the form of monoclonal anti-Tau antibodies, and active anti-Tau immunotherapy.

11. The method according to claim 1, wherein the low dose of IL-2 is administered for a chronic treatment during at least three consecutive days.

12. The method according to claim 1, wherein the treatment comprises:
a first course of administration wherein a low dose of IL-2 of 0.2 MUI/m$^2$ is administered once a day for 1 to 10 consecutive days, and
a second course of administration wherein a low dose of IL-2 of 0.2 MUI/m$^2$/day is administered after one to three weeks following the first course of administration.

13. The method according to claim 1, wherein the treatment comprises:
a first course of administration wherein a low dose of IL-2 of 0.6 MUI/m$^2$ is administered once a day for 1 to 10 consecutive days, and
a second course of administration wherein a low dose of IL-2 of 0.6 MUI/m$^2$/day is administered after two to four weeks following the first course of administration.

14. The method according to claim 1, wherein the treatment comprises:
a first course of administration wherein a low dose of IL-2 of 0.6 MUI/m$^2$ is administered once a day for 1 to 10 consecutive days, and
a second course of administration wherein a low dose of IL-2 of 0.6 MUI/m$^2$/day is administered after two to four weeks following the first course of administration, wherein said second course of administration is repeated every two to four weeks.

15. The method according to claim 1, wherein the treatment comprises:
a first course of administration wherein a low dose of IL-2 of 1.8 MUI/m$^2$ is administered once a day for 1 to 10 consecutive days, and
a second course of administration wherein a low dose of IL-2 of 1.8 MUI/m$^2$/day is administered after one to two months following the first course of administration.

16. The method according to claim 1, wherein the treatment improves cognitive function.

17. The method according to claim 1, wherein the treatment reduces non-cognitive neurobehavioral deficits.

18. The method according to claim 1, wherein IL-2 is administered at a pre-dementia stage, at a pro-dromal stage, at a mild dementia stage or at a moderate dementia stage.

19. The method according to claim 1, wherein amyloid peptide, Tau protein and/or phosphorylated Tau protein has been detected in the subject.

20. A method for delaying an onset of cognitive deficits caused by Alzheimer's disorder in a subject in need thereof comprising administering a therapeutically effective amount of a booster of Treg cells, wherein the booster of Treg cells is a low dose of IL-2, and wherein a low dose of IL-2 is at a range below 3.5 MIU/m2/day, and wherein IL-2 is administered prior to cognitive deficits.

21. The method according to claim 20, wherein the low dose of IL-2 is administered to the subject prior to, concurrent to, or subsequent to other active agent(s) for treating an Alzheimer's disorder and/or side effects of said active agent(s).

22. The method according to claim 20, wherein the low dose of IL-2 is administered to the subject in need thereof by subcutaneous, intramuscular, intravenous, intraocular, transdermal, topical, parenteral, rectal, intranasal or oral administration.

23. The method according to claim 20, wherein the subject has a genetic mutation associated with an Alzheimer's disorder.

24. The method according to claim 20, wherein the subject is affected with an early-onset variant of an Alzheimer's disorder.

25. The method according to claim 20, wherein the low dose of IL-2 is at a range of 0.05 to 2 MIU/m$^2$/day.

26. The method according to claim 20, wherein the low dose of IL-2 is at a range of 0.2 to 1 MIU/m$^2$/day.

27. The method according to claim 20, wherein the low dose of IL-2 is administered in a sustained-release form.

28. The method according to claim 20, wherein the low dose of IL-2 is administered to the subject prior to, concurrent to, or subsequent to other active agent(s) for treating an Alzheimer's disorder and/or side effects of said active agent(s), the other active agent(s) for treating an Alzheimer's disorder being selected from the group consisting of a cholinesterase inhibitor, a N-methyl D-aspartate antagonist, a BACE1 inhibitor, a γ secretase inhibitor, passive anti-Aβ immunotherapy in the form of monoclonal anti-Aβ antibodies, active anti-Aβ immunotherapy, non-steroidal anti-inflammatory drugs, passive anti-Tau immunotherapy in the form of monoclonal anti-Tau antibodies, and an active anti-Tau immunotherapy.

29. The method according to claim 20, wherein the low dose of IL-2 is administered for a chronic treatment during at least three consecutive days.

30. The method according to claim 20, wherein the treatment comprises:
a first course of administration wherein a low dose of IL-2 of 0.2 MUI/m$^2$ is administered once a day for 1 to 10 consecutive days, and
a second course of administration wherein a low dose of IL-2 of 0.2 MUI/m$^2$/day is administered after one to three weeks following the first course of administration.

31. The method according to claim 20, wherein the treatment comprises:
a first course of administration wherein a low dose of IL-2 of 0.6 MUI/m² is administered once a day for 1 to 10 consecutive days, and
a second course of administration wherein a low dose of IL-2 of 0.6 MUI/m²/day is administered after two to four weeks following the first course of administration.

32. The method according to claim 20, wherein the treatment comprises:
a first course of administration wherein a low dose of IL-2 of 0.6 MUI/m² is administered once a day for 1 to 10 consecutive days, and
a second course of administration wherein a low dose of IL-2 of 0.6 MUI/m²/day is administered after two to four weeks following the first course of administration, wherein said second course of administration is repeated every two to four weeks.

33. The method according to claim 20, wherein the treatment comprises:
a first course of administration wherein a low dose of IL-2 of 1.8 MUI/m² is administered once a day for 1 to 10 consecutive days, and
a second course of administration wherein a low dose of IL-2 of 1.8 MUI/m²/day is administered after one to two months following the first course of administration.

34. The method according to claim 20, wherein amyloid peptide, Tau protein and/or phosphorylated Tau protein has been detected in the subject.

35. The method according to claim 20, wherein the treatment reduces non-cognitive neurobehavioral deficits.

36. A method for delaying progression of an Alzheimer's disorder in a subject in need thereof comprising administering a therapeutically effective amount of a booster of Treg cells, wherein the booster of Treg cells is a low dose of IL-2, and wherein a low dose of IL-2 is at a range below 3.5 MIU/m2/day, and wherein IL-2 is administered at a stage of mild cognitive impairment.

37. The method according to claim 36, wherein the low dose of IL-2 is administered to the subject prior to, concurrent to, or subsequent to other active agent(s) for treating an Alzheimer's disorder and/or side effects of said active agent(s).

38. The method according to claim 36, wherein the low dose of IL-2 is administered to the subject in need thereof by subcutaneous, intramuscular, intravenous, intraocular, transdermal, topical, parenteral, rectal, intranasal or oral administration.

39. The method according to claim 36, wherein the subject is at an early stage of Alzheimer's disorder.

40. The method according to claim 36, wherein the subject is diagnosed with an Alzheimer's disorder.

41. The method according to claim 36, wherein the subject has a genetic mutation associated with an Alzheimer's disorder.

42. The method according to claim 36, wherein the subject is affected with an early-onset variant of an Alzheimer's disorder.

43. The method according to claim 36, wherein the subject has been diagnosed with an early-onset variant of an Alzheimer's disorder.

44. The method according to claim 36, wherein the low dose of IL-2 is at a range of 0.05 to 2 MIU/m²/day.

45. The method according to claim 36, wherein the low dose of IL-2 is at a range of 0.2 to 1 MIU/m²/day.

46. The method according to claim 36, wherein the low dose of IL-2 is administered in a sustained-release form.

47. The method according to claim 36, wherein the low dose of IL-2 is administered to the subject prior to, concurrent to, or subsequent to other active agent(s) for treating an Alzheimer's disorder and/or side effects of said active agent(s), the other active agent(s) for treating an Alzheimer's disorder being selected from the group consisting of a cholinesterase inhibitor, a N-methyl D-aspartate antagonist, a BACE1 inhibitor, a γ secretase inhibitor, passive anti-Aβ immunotherapy in the form of monoclonal anti-Aβ antibodies, active anti-Aβ immunotherapy, non-steroidal anti-inflammatory drugs, passive anti-Tau immunotherapy in the form of monoclonal anti-Tau antibodies, and an active anti-Tau immunotherapy.

48. The method according to claim 36, wherein the low dose of IL-2 is administered for a chronic treatment during at least three consecutive days.

49. The method according to claim 36, wherein the treatment comprises:
a first course of administration wherein a low dose of IL-2 of 0.2 MUI/m² is administered once a day for 1 to 10 consecutive days, and
a second course of administration wherein a low dose of IL-2 of 0.2 MUI/m²/day is administered after one to three weeks following the first course of administration.

50. The method according to claim 36, wherein the treatment comprises:
a first course of administration wherein a low dose of IL-2 of 0.6 MUI/m² is administered once a day for 1 to 10 consecutive days, and
a second course of administration wherein a low dose of IL-2 of 0.6 MUI/m²/day is administered after two to four weeks following the first course of administration.

51. The method according to claim 36, wherein the treatment comprises:
a first course of administration wherein a low dose of IL-2 of 0.6 MUI/m² is administered once a day for 1 to 10 consecutive days, and
a second course of administration wherein a low dose of IL-2 of 0.6 MUI/m²/day is administered after two to four weeks following the first course of administration, wherein said second course of administration is repeated every two to four weeks.

52. The method according to claim 36, wherein the treatment comprises:
a first course of administration wherein a low dose of IL-2 of 1.8 MUI/m² is administered once a day for 1 to 10 consecutive days, and
a second course of administration wherein a low dose of IL-2 of 1.8 MUI/m²/day is administered after one to two months following the first course of administration.

53. The method according to claim 36, wherein IL-2 is administered at a pro-dromal stage.

54. The method according to claim 36, wherein the treatment improves cognitive function.

55. The method according to claim 36, wherein the treatment reduces non-cognitive neurobehavioral deficits.

56. The method according to claim 36, wherein amyloid peptide, Tau protein and/or phosphorylated Tau protein has been detected in the subject.

* * * * *